`US006656946B2`

United States Patent
Himmelsbach et al.

(10) Patent No.: US 6,656,946 B2
(45) Date of Patent: Dec. 2, 2003

(54) AMINOQUINAZOLINES WHICH INHIBIT SIGNAL TRANSDUCTION MEDIATED BY TYROSINE KINASES

(75) Inventors: Frank Himmelsbach, Mittelbiberach (DE); Elke Langkopf, Warthausen (DE); Birgit Jung, Schwabenheim (DE); Stefan Blech, Warthausen (DE); Flavio Solca, Vienna (AT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/934,772

(22) Filed: Aug. 22, 2001

(65) Prior Publication Data

US 2002/0082271 A1 Jun. 27, 2002

Related U.S. Application Data

(60) Provisional application No. 60/230,035, filed on Sep. 5, 2000.

(30) Foreign Application Priority Data

Aug. 26, 2000 (DE) .......................... 100 42 058

(51) Int. Cl.⁷ .................... A61K 31/517; A61K 31/535; A61P 11/06; C07D 295/02; C07D 239/70
(52) U.S. Cl. .............. 514/266.4; 514/233.5; 514/255; 514/266.1; 514/312; 544/107; 544/253; 544/363
(58) Field of Search ................ 514/233.5, 255, 514/266.1, 266.4, 312; 544/107, 253, 363

(56) References Cited

U.S. PATENT DOCUMENTS 6,362,336 B1 * 3/2002 Lohmann et al. .......... 544/283
6,414,148 B1 * 7/2002 Thomas et al. ............. 544/283

FOREIGN PATENT DOCUMENTS

| EP | 0 787 722 A1 | 8/1997 |
|---|---|---|
| WO | WO 96 33980 A1 | 10/1996 |
| WO | WO 97 22596 A | 6/1997 |
| WO | WO 97 30035 A1 | 8/1997 |
| WO | WO 97 32856 A1 | 9/1997 |
| WO | WO 98 13354 A1 | 4/1998 |
| WO | WO 99 01467 | 1/1999 |
| WO | WO 99 09016 A1 | 2/1999 |
| WO | WO 00 18740 A1 | 4/2000 |
| WO | WO 00 55141 A1 | 9/2000 |

OTHER PUBLICATIONS

Boschelli; "Small molecule inhibitors of receptor tyrosine kinases"; Review Article—Chemical Sciences, 2001.

* cited by examiner

Primary Examiner—Mukund J. Shah
Assistant Examiner—Tamthom N. Truong
(74) Attorney, Agent, or Firm—Robert P. Raymond; Alan R. Stempel; Mary-Ellen M. Devlin

(57) ABSTRACT

Compounds of the formula (I)

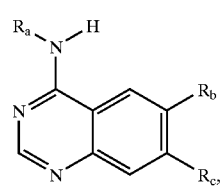

having an inhibitory effect on signal transduction mediated by tyrosine kinases and their use in the treatment of diseases, especially tumoral diseases and diseases of the lungs and airways, and the preparation thereof.

6 Claims, No Drawings

AMINOQUINAZOLINES WHICH INHIBIT SIGNAL TRANSDUCTION MEDIATED BY TYROSINE KINASES

RELATED APPLICATIONS

Benefit of U.S. Provisional Application Serial No. 60/230,035, filed on Sep. 5, 2000 is hereby claimed.

DESCRIPTION OF THE INVENTION

The present invention relates to bicyclic heterocycles of general formula

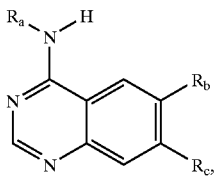

(I)

the tautomers, the stereoisomers and the salts thereof, particularly the physiologically acceptable salts thereof with inorganic or organic acids or bases which have valuable pharmacological properties, particularly an inhibitory effect on signal transduction mediated by tyrosine kinases, the use thereof for treating diseases, particularly tumoral diseases, diseases of the lungs and respiratory tract, and the preparation thereof.

In the above general formula I $R_a$ denotes a benzyl or 1-phenylethyl group or a phenyl group substituted by the groups $R_1$ and $R_2$, where $R_1$ denotes a hydrogen, fluorine, chlorine or bromine atom, a methyl, trifluoromethyl, cyano or ethynyl group and $R_2$ denotes a hydrogen or fluorine atom, one of the groups $R_b$ or $R_c$ denotes an $R_3$—$(CH_2)_m$—O group and the other group $R_b$ or $R_c$ denotes a methoxy, cyclobutyloxy, cyclopentyloxy, cyclopropylmethoxy, cyclobutylmethoxy, cyclopentylmethoxy, tetrahydrofuran-3-yloxy, tetrahydropyran-3-yloxy, tetrahydropyran-4-yloxy, tetrahydrofuranylmethoxy or tetrahydropyranylmethoxy group, where $R_3$ denotes an N-(2-oxo-tetrahydrofuran-4-yl)-methylamino or N-(2-oxo-tetrahydrofuran-4-yl)-ethylamino group, an $R_4$—O—CO—$CH_2$—N—$CH_2CH_2$—OH group substituted at the methylene groups by one or two methyl or ethyl groups, wherein $R_4$ represents a hydrogen atom or a $C_{1-4}$-alkyl group, or a 2-oxo-morpholin-4-yl group substituted by one or two methyl or ethyl groups and m denotes the number 2, 3 or 4, with the proviso that the compounds 4-[(3-chloro-4-fluorophenyl)amino]-6-cyclopentyloxy-7-(2-{N-(2-hydroxy-2-methyl-prop-1-yl)-N-[(ethoxycarbonyl)methyl]-amino}-ethoxy)-quinazoline, 4-[(3-chloro-4-fluorophenyl)amino]-6-cyclopentyloxy-7-[2-(6,6-dimethyl-2-oxo-morpholin-4-yl)-ethoxy]-quinazoline, 4-[(3-bromo-phenyl)amino]-6-[2-(6,6-dimethyl-2-oxo-morpholin-4-yl)-ethoxy]-7-methoxy-quinazoline and 4-[(3-bromo-phenyl)amino]-6-{2-[N-(2-oxo-tetrahydrofuran-4-yl)-N-methyl-amino]-thoxy}-7-methoxy-quinazoline are excluded, the tautomers, the stereoisomers and the salts thereof.

Preferred compounds of the above general formula I are those wherein $R_a$ denotes a benzyl or 1-phenylethyl group or a phenyl group substituted by the groups $R_1$ and $R_2$, where $R_1$ denotes a hydrogen, fluorine, chlorine or bromine atom, a methyl, trifluoromethyl, cyano or ethynyl group and $R_2$ denotes a hydrogen or fluorine atom, one of the groups $R_b$ or $R_c$ denotes a $R_3$—$(CH_2)_m$—O group and the other group $R_b$ or $R_c$ denotes a methoxy, cyclobutyloxy, cyclopentyloxy, cyclopropylmethoxy, cyclobutylmethoxy, cyclopentylmethoxy, tetrahydrofuran-3-yloxy, tetrahydropyran-3-yloxy, tetrahydropyran-4-yloxy, tetrahydrofuranylmethoxy or tetrahydropyranylmethoxy group, where $R_3$ denotes an N-(2-oxo-tetrahydrofuran-4-yl)-methylamino or N-(2-oxo-tetrahydrofuran-4-yl)-ethylamino group, an $R_4$—O—CO—$CH_2$—N—$CH_2CH_2$—OH group substituted at the methylene groups by one or two methyl or ethyl groups wherein $R_4$ represents a hydrogen atom or a $C_{1-4}$-alkyl group, or a 2-oxo-morpholin-4-yl group substituted by one or two methyl or ethyl groups and m represents the number 2, 3 or 4, with the proviso that the compounds 4-[(3-chloro-4-fluorophenyl)amino]-6-cyclopentyloxy-7-(2-{N-(2-hydroxy-2-methyl-prop-1-yl)-N-[(ethoxycarbonyl)methyl]-amino}-ethoxy)-quinazoline, 4-[(3-chloro-4-fluorophenyl)amino]-6-cyclopentyloxy-7-[2-(6,6-dimethyl-2-oxo-morpholin-4-yl)-ethoxy]-quinazoline, 4-[(3-bromo-phenyl)amino]-6-[2-(6,6-dimethyl-2-oxo-morpholin-4-yl)-ethoxy]-7-methoxy-quinazoline, 4-[(3-bromo-phenyl)amino]-6-{2-[N-(2-oxo-tetrahydrofuran-4-yl)-N-methyl-amino]-ethoxy}-7-methoxy-quinazoline, 4-[(3-bromo-phenyl)amino]-6-(2-{N-(2-hydroxy-2-methyl-prop-1-yl)-N-[(ethoxycarbonyl)methyl]-amino}-ethoxy)-7-methoxy-quinazoline, 4-[(3-bromo-phenyl)amino]-6-[2-(3-methyl-2-oxo-morpholin-4-yl)ethoxy)-7-methoxy-quinazoline, 4-[(3-bromo-phenyl)amino]-6-[2-(5, 5-dimethyl-2-oxo-morpholin-4-yl)ethoxy]-7-methoxy-quinazoline, 4-[(3-chloro-4-fluorophenyl)amino]-6-[2-(6,6-dimethyl-2-oxo-morpholin-4-yl)-ethoxy]-7-methoxy-quinazoline, 4-[(3-chloro-4-fluorophenyl)amino]-6-[2-(6,6-dimethyl-2-oxo-morpholin-4-yl)-ethoxy]-7-cyclobutyloxy-quinazoline, 4-[(3-chloro-4-fluorophenyl)amino]-6-[2-(6,6-dimethyl-2-oxo-morpholin-4-yl)-ethoxy]-7-cyclopentyloxy-quinazoline, 4-[(3-chloro-4-fluorophenyl)amino]-6-[2-(6,6-dimethyl-2-oxo-morpholin-4-yl)-ethoxy]-7-cyclopropylmethoxy-quinazoline, 4-[(3-chloro-4-fluorophenyl]amino]-6-[2-(6,6-dimethyl-2-oxo-morpholin-4-yl)-ethoxy]-7-cyclopentylmethoxy-quinazoline, 4-[(3-chloro-4-fluorophenyl)amino]-6-{2-[N-(2-oxo-tetrahydrofuran-4-yl)-N-methyl-amino]-ethoxy}-7-methoxy-quinazoline, 4-[(3-chloro-4-fluorophenyl)amino]-6-{2-[N-(2-oxo-tetrahydrofuran-4-yl)-N-methyl-amino]-ethoxy}-7-cyclopentyloxy-quinazoline, 4-[(3-chloro-4-fluorophenyl)amino]-6-{2-[N-(2-oxo-tetrahydrofuran-4-yl)-N-methyl-amino]-ethoxy}-7-cyclopentylmethoxy-quinazoline, 4-[(3-chloro-4-fluorophenyl)amino]-6-[3-(6,6-dimethyl-2-oxo-morpholin-4-yl)-propyloxy]-7-methoxy-quinazoline, 4-[(3-chloro-4-fluorophenyl)amino]-6-[3-(6,6-dimethyl-2-oxo-morpholin-4-yl)-propyloxy]-7-cyclopentyloxy-quinazoline, 4-[(3-chloro-4-fluorophenyl)amino]-6-[3-(6,6-dimethyl-2-oxo-morpholin-4-yl)-propyloxy]-7-cyclopentylmethoxy-quinazoline, (R)-4-[(1-phenyl-ethyl)amino]-6-[3-(6,6-dimethyl-2-oxo-morpholin-4-yl)-propyloxy]-7-cyclopentyloxy-quinazoline, 4-[(3-chloro-4-fluorophenyl)amino]-7-[2-(6,6-dimethyl-2-oxo-morpholin-4-yl)-ethoxy]-6-methoxy-quinazoline, 4-[(3-chloro-4-fluorophenyl)amino]-7-[2-(6,6-dimethyl-2-oxo-morpholin-4-yl)-ethoxy]-6-cyclobutyloxy-quinazoline, 4-[(3-chloro-4-fluorophenyl)amino]-7-[2-(6,6-dimethyl-2-oxo-morpholin-4-yl)-ethoxy]-6-cyclopentyloxy-quinazoline, 4-[(3-chloro-4-fluorophenyl)amino]-7-[2-(6,6-dimethyl-2-oxo-morpholin-4-yl)-ethoxy]-6-cyclopropylmethoxy-quinazoline, 4-[(3-chloro-4-fluorophenyl)amino]-7-[2-(6,6-dimethyl-2-oxo-morpholin-4-yl)-ethoxy]-6-cyclopentylmethoxy-quinazoline, 4-[(3-chloro-4-fluorophenyl)amino]-7-{2-[N-(2-oxo-tetrahydrofuran-4-yl)-N-methyl-amino]-ethoxy}-6-methoxy-quinazoline, 4-[(3-chloro-4-fluorophenyl)amino]-7-{2-[N-(2-oxo-tetrahydrofuran-4-yl)-N-methyl-amino]-ethoxy}-6-cyclopentyloxy-quinazoline, 4-[(3-chloro-4-fluorophenyl)amino]-7-{2-[N-(2-oxo-tetrahydrofuran-4-yl)-N-methyl-amino]-ethoxy}-6-cyclopentylmethoxy-quinazoline, 4-[(3-chloro-4-fluorophenyl)amino]-7-[3-(6,6-dimethyl-2-oxo-morpholin-4-yl)-propyloxy]-6-methoxy-quinazoline, 4-[(3-chloro-4-fluorophenyl)amino]-7-[3-(6,6-dimethyl-2-oxo-morpholin-4-yl)-propyloxy]-6-cyclopentyloxy-quinazoline, 4-[(3-chloro-4-fluorophenyl)amino]-7-[3-(6,6-dimethyl-2-oxo-morpholin-4-yl)-propyloxy]-6-cyclopentylmethoxy-quinazoline and (R)4-[(1-phenyl-ethyl)amino]-7-[3-(6,6-dimethyl-2-oxo-morpholin-4-yl)-propyloxy]-6-cyclopentyloxy-quinazoline are excluded, particularly those wherein $R_a$ represents a 1-phenylethyl group or a phenyl group substituted by the groups $R_1$ and $R_2$, where
 $R_1$ represents a fluorine, chlorine or bromine atom, a methyl or ethynyl group and $R_2$ denotes a hydrogen or fluorine atom,
one of the groups $R_b$ or $R_c$ represents a $R_3$—$(CH_2)_m$—O group and the other group $R_b$ or $R_c$ represents a methoxy, cyclobutyloxy, cyclopentyloxy, cyclopropylmethoxy, cyclobutylmethoxy, cyclopentylmethoxy, tetrahydrofuran-3-yloxy, tetrahydropyran-3-yloxy, tetrahydropyran-4-yloxy, tetrahydrofuranylmethoxy or tetrahydropyranylmethoxy group, where
 $R_3$ represents an N-(2-oxo-tetrahydrofuran-4-yl)-methylamino group, an $R_4$—O—CO—$CH_2$—N—$CH_2CH_2$—OH group substituted at the methylene groups by one or two methyl groups, wherein
  $R_4$ represents a $C_{1-4}$-alkyl group,
 or a 2-oxo-morpholin-4-yl group substituted by one or two methyl groups and
m represents the number 2, 3 or 4, with the proviso that the compounds 4-[(3-chloro-4-fluorophenyl)amino]-6-cyclopentyloxy-7-(2-{N-(2-hydroxy-2-methyl-prop-1-yl)-N-[(ethoxycarbonyl)methyl]-amino}-ethoxy)-quinazoline, 4-[(3-chloro-4-fluorophenyl)amino]-6-cyclopentyloxy-7-[2-(6,6-dimethyl-2-oxo-morpholin-4-yl)-ethoxy]-quinazoline, 4-[(3-bromo-phenyl)amino]-6-[2-(6,6-dimethyl-2-oxo-morpholin-4-yl)-ethoxy]-7-methoxy-quinazoline, 4-[(3-bromo-phenyl)amino]-6-{2-[N-(2-oxo-tetrahydrofuran-4-yl)-N-methyl-amino]-ethoxy}-7-methoxy-quinazoline, 4-[(3-bromo-phenyl)amino]-6-(2-{N-(2-hydroxy-2-methyl-prop-1-yl)-N-[(ethoxycarbonyl)methyl]-amino}-ethoxy)-7-methoxy-quinazoline, 4-[(3-bromo-phenyl)amino]-6-[2-(3-methyl-2-oxo-morpholin-4-yl)ethoxy]-7-methoxy-quinazoline, 4-[(3-bromo-phenyl)amino]-6-[2-(5,5-dimethyl-2-oxo-morpholin-4-yl)ethoxy]-7-methoxy-quinazoline, 4-[(3-chloro-4-fluorophenyl)amino]-6-[2-(6,6-dimethyl-2-oxo-morpholin-4-yl)-ethoxy]-7-methoxy-quinazoline, 4-[(3-chloro-4-fluorophenyl)amino]-6-[2-(6,6-dimethyl-2-oxo-morpholin-4-yl)-ethoxy]-7-cyclobutyloxy-quinazoline, 4-[(3-chloro-4-fluorophenyl)amino]-6-[2-(6,6-dimethyl-2-oxo-morpholin-4-yl)-ethoxy]-7-cyclopentyloxy-quinazoline, 4-[(3-chloro-4-fluorophenyl)amino]-6-[2-(6,6-dimethyl-2-oxo-morpholin-4-yl)-ethoxy]-7-cyclopropylmethoxy-quinazoline, 4-[(3-chloro-4-fluorophenyl)amino]-6-[2-(6,6-dimethyl-2-oxo-morpholin-4-yl)-ethoxy]-7-cyclopentylmethoxy-quinazoline, 4-[(3-chloro-4-fluorophenyl)amino]-6-{2-[N-(2-oxo-tetrahydrofuran-4-yl)-N-methyl-amino]-ethoxy}-7-methoxy-quinazoline, 4-[(3-chloro-4-fluorophenyl)amino]-6-{2-[N-(2-oxo-tetrahydrofuran-4-yl)-N-methyl-amino]-ethoxy}-7-cyclopentyloxy-quinazoline, 4-[(3-chloro-4-fluorophenyl)amino]-6-{ 2-[N-(2-oxo-tetrahydrofuran-4-yl)-N-methyl-amino]-ethoxy}-7-cyclopentylmethoxy-quinazoline, 4-[(3-chloro-4-fluorophenyl)amino]-6-[3-(6,6-dimethyl-2-oxo-morpholin-4-yl)-propyloxy]-7-methoxy-quinazoline, 4-[(3-chloro-4-fluorophenyl)amino]-6-[3-(6,6-dimethyl-2-oxo-morpholin-4-yl)-propyloxy]-7-cyclopentyloxy-quinazoline, 4-[(3-chloro-4-fluorophenyl)amino]-6-[3-(6,6-dimethyl-2-oxo-morpholin-4-yl)-propyloxy]-7-cyclopentylmethoxy-quinazoline, (R)4-[(1-phenyl-ethyl)amino]-6-[3-(6,6-dimethyl-2-oxo-morpholin-4-yl)-propyloxy]-7-cyclopentyloxy-quinazoline, 4-[(3-chloro-4-fluorophenyl)amino]-7-[2-(6,6-dimethyl-2-oxo-morpholin-4-yl)-ethoxy-6-methoxy-quinazoline, 4-[(3-chloro-4-fluorophenyl)amino]-7-[2-(6,6-dimethyl-2-oxo-morpholin-4-yl)-ethoxy]-6-cyclobutyloxy-quinazoline, 4-[(3-chloro-4-fluorophenyl)amino]-7-[2-(6,6-dimethyl-2-oxo-morpholin-4-yl)-ethoxy]-6-cyclopentyloxy-quinazoline, 4-[(3-chloro-4-fluorophenyl)amino]-7-[2-(6,6-dimethyl-2-oxo-morpholin-4-yl)-ethoxy]-6-cyclopropylmethoxy-quinazoline, 4-[(3-chloro-4-fluorophenyl)amino]-7-[2-(6,6-dimethyl-2-oxo-morpholin-4-yl)-ethoxy]-6-cyclopentylmethoxy-quinazoline, 4-[(3-chloro-4-fluorophenyl)amino]-7-{2-[N-(2-oxo-tetrahydrofuran-4-yl)-N-methyl-amino]-ethoxy}-6-methoxy-quinazoline, 4-[(3-chloro-4-fluorophenyl)amino]-7-{2-[N-(2-oxo-tetrahydrofuran-4-yl)-N-methyl-amino]-ethoxy}-6-cyclopentyloxy-quinazoline, 4-[(3-chloro-4-fluorophenyl)amino]-7-{2-[N-(2-oxo-tetrahydrofuran-4-yl)-N-methyl-amino]-ethoxy}-6-cyclopentylmethoxy-quinazoline, 4-[(3-chloro-4-fluorophenyl)amino]-7-[3-(6,6-dimethyl-2-oxo-morpholin-4-yl)-propyloxy]-6-methoxy-quinazoline, 4-[(3-chloro-4-fluorophenyl)amino]-7-[3-(6,6-dimethyl-2-oxo-morpholin-4-yl)-propyloxy]-6-cyclopentyloxy-quinazoline, 4-[(3-chloro-4-fluorophenyl)amino]-7-[3-(6,6-dimethyl-2-oxo-morpholin-4-yl)-propyloxy]-6-cyclopentylmethoxy-quinazoline and (R)4-[(1-phenyl-ethyl)amino]-7-[3-(6,6-dimethyl-2-oxo-morpholin-4-yl)-propyloxy]-6-cyclopentyloxy-quinazoline are excluded, the tautomers, the stereoisomers and the salts thereof.

Particularly preferred compounds of general formula I are those wherein $R_a$ represents a 1-phenylethyl group or a phenyl group substituted by the groups $R_1$ and $R_2$, where $R_1$ denotes a fluorine, chlorine or bromine atom and $R_2$ denotes a hydrogen or fluorine atom, one of the groups $R_b$ or $R_c$ denotes a $R_3$—$(CH_2)_m$—O group and the other group $R_b$ or $R_c$ denotes a methoxy, cyclobutyloxy, cyclopentyloxy, cyclopropylmethoxy, cyclobutylmethoxy, cyclopentylmethoxy, tetrahydrofuran-3-yloxy, tetrahydropyran-3-yloxy, tetrahydropyran-4-yloxy, tetrahydrofuranylmethoxy or tetrahydropyranylmethoxy group, where $R_3$ denotes an N-(2-oxo-tetrahydrofuran-4-yl)-methylamino group or a 2-oxo-morpholin-4-yl group substituted by one or two methyl groups and m represents the number 2, 3 or 4, with the proviso that the compounds 4-[(3-chloro-4-fluorophenyl)amino]-6-cyclopentyloxy-7-[2-(6,6-dimethyl-2-oxo-morpholin-4-yl)-ethoxy]-quinazoline, 4-[(3-bromo-phenyl)amino]-6-[2-(6,6-dimethyl-2-oxo-morpholin-4-yl)-ethoxy]-7-methoxy-quinazoline, 4-[(3-bromo-phenyl)amino]-6-{2-[N-(2-oxo-tetrahydrofuran-4-yl)-N-methyl-amino]-ethoxy}-7-methoxy-quinazoline, 4-[(3-bromo-phenyl)amino]-6-[2-(3-methyl-2-oxo-morpholin-4-yl)ethoxy]-7-methoxy-quinazoline, 4-[(3-bromo-phenyl)amino]-6-[2-(5,5-dimethyl-2-oxo-morpholin-4-yl)ethoxy]-7-methoxy-quinazoline, 4-[(3-chloro-4-fluorophenyl)amino]-6-[2-(6,6-dimethyl-2-oxo-morpholin-4-yl)-ethoxy]-7-methoxy-quinazoline, 4-[(3-chloro-4-fluorophenyl)amino]-6-[2-(6,6-dimethyl-2-oxo-morpholin-4-yl)-ethoxy]-7-cyclobutyloxy-quinazoline, 4-[(3-chloro-4-fluorophenyl)amino]-6-[2-(6,6-dimethyl-2-oxo-morpholin-4-yl)-ethoxy]-7-cyclopentyloxy-quinazoline, 4-[(3-chloro-4-fluorophenyl)amino]-6-[2-(6,6-dimethyl-2-oxo-morpholin-4-yl)-ethoxy]-7-cyclopropylmethoxy-quinazoline, 4-[(3-chloro-4-fluorophenyl]amino]-6-[2-(6,6-dimethyl-2-oxo-morpholin-4-yl)-ethoxy]-7-cyclopentylmethoxy-quinazoline, 4-[(3-chloro-4-fluorophenyl)amino]-6-{2-[N-(2-oxo-tetrahydrofuran-4-yl)-N-methyl-amino]-ethoxy}-7-methoxy-quinazoline, 4-[(3-chloro-4-fluorophenyl)amino]-6-{2-[N-(2-oxo-tetrahydrofuran-4-yl)-N-methyl-amino]-ethoxy}-7-cyclopentyloxy-quinazoline, 4-[(3-chloro-4-fluorophenyl)amino]-6-{2-[N-(2-oxo-tetrahydrofuran-4-yl)-N-methyl-amino]-ethoxy}-7-cyclopentylmethoxy-quinazoline, 4-[(3-chloro-4-fluorophenyl)amino]-6-[3-(6,6-dimethyl-2-oxo-morpholin-4-yl)-propyloxy]-7-methoxy-quinazoline, 4-[(3-chloro-4-fluorophenyl)amino]-6-[3-(6,6-dimethyl-2-oxo-morpholin-4-yl)-propyloxy]-7-cyclopentyloxy-quinazoline, 4-[(3-chloro-4-fluorophenyl)amino]-6-[3-(6,6-dimethyl-2-oxo-morpholin-4-yl)-propyloxy]-7-cyclopentylmethoxy-quinazoline, (R)4-[(1-phenyl-ethyl)amino]-6-[3-(6,6-dimethyl-2-oxo-morpholin-4-yl)-propyloxy]-7-cyclopentyloxy-quinazoline, 4-[(3-chloro-4-fluorophenyl)amino]-7-[2-(6,6-dimethyl-2-oxo-morpholin-4-yl)-ethoxy]-6-methoxy-quinazoline, 4-[(3-chloro-4-fluorophenyl)amino]-7-[2-(6,6-dimethyl-2-oxo-morpholin-4-yl)-ethoxy]-6-cyclobutyloxy-quinazoline, 4-[(3-chloro-4-fluorophenyl)amino]-7-[2-(6,6-dimethyl-2-oxo-morpholin-4-yl)-ethoxy]-6-cyclopentyloxy-quinazoline, 4-[(3-chloro-4-fluorophenyl)amino]-7-[2-(6,6-dimethyl-2-oxo-morpholin-4-yl)-ethoxy]-6-cyclopropylmethoxy-quinazoline, 4-[(3-chloro-4-fluorophenyl)amino]-7-[2-(6,6-dimethyl-2-oxo-morpholin-4-yl)-ethoxy]-6-cyclopentylmethoxy-quinazoline, 4-[(3-chloro-4-fluorophenyl)amino]-7-{2-[N-(2-oxo-tetrahydrofuran-4-yl)-N-methyl-amino]-ethoxy}-6-methoxy-quinazoline, 4-[(3-chloro-4-fluorophenyl)amino]-7-{2-[N-(2-oxo-tetrahydrofuran-4-yl)-N-methyl-amino]-ethoxy}-6-cyclopentyloxy-quinazoline, 4-[(3-chloro-4-fluorophenyl)amino]-7-{2-[N-(2-oxo-tetrahydrofuran-4-yl)-N-methyl-amino]-ethoxy}-6-cyclopentylmethoxy-quinazoline, 4-[(3-chloro-4-fluorophenyl)amino]-7-[3-(6,6-dimethyl-2-oxo-morpholin-4-yl)-propyloxy]-6-methoxy-quinzoline, 4-[(3-chloro-4-fluorophenyl)amino]-7-[3-(6,6-dimethyl-2-oxo-morpholin-4-yl)-propyloxy]-6-cyclopentyloxy-quinazoline, 4-[(3-chloro-4-fluorophenyl)amino]-7-[3-(6,6-dimethyl-2-oxo-morpholin-4-yl)-propyloxy]-6-cyclopentylmethoxy-quinazoline and (R)4-[(1-phenyl-ethyl)amino]-7-[3-(6,6-dimethyl-2-oxo-morpholin-4-yl)-propyloxy]-6-cyclopentyloxy-quinazoline are excluded, the tautomers, the stereoisomers and the salts thereof.

Most particularly preferred compounds of general formula I are those wherein $R_a$ denotes a 1-phenylethyl, 3-bromophenyl or 3-chloro-4-fluorophenyl group, $R_b$ denotes a $R_3$—$(CH_2)_m$—O group, wherein
$R_3$ denotes a 2-oxo-morpholin-4-yl group substituted by one or two methyl groups and
m denotes the number 2 or 3, and $R_c$ denotes a methoxy, cyclobutyloxy, cyclopentyloxy, cyclopropylmethoxy, tetrahydrofuran-3-yloxy or tetrahydrofuranylmethoxy group, with the proviso that the compounds 4-[(3-bromo-phenyl)amino]-6-[2-(6,6-dimethyl-2-oxo-morpholin-4-yl)-ethoxy]-7-methoxy-quinazoline, 4-[(3-bromo-phenyl)amino]-6-[2-(3-methyl-2-oxo-morpholin-4-yl)ethoxy]-7-methoxy-quinazoline, 4-[(3-bromo-phenyl)amino]-6-[2-(5,5-dimethyl-2-oxo-morpholin-4-yl)ethoxy]-7-methoxy-quinazoline, 4-[(3-chloro-4-fluorophenyl)amino]-6-[2-(6,6-dimethyl-2-oxo-morpholin-4-yl)-ethoxy]-7-methoxy-quinazoline, 4-[(3-chloro-4-fluorophenyl)amino]-6-[2-(6,6-dimethyl-2-oxo-morpholin-4-yl)-ethoxy]-7-cyclobutyloxy-quinazoline, 4-[(3-chloro-4-fluorophenyl)amino]-6-[2-(6,6-dimethyl-2-oxo-morpholin-4-yl)-ethoxy]-7-cyclopropylmethoxy-quinazoline, 4-[(3-chloro-4-fluorophenyl)amino]-6-[3-(6,6-dimethyl-2-oxo-morpholin-4-yl)-propyloxy]-7-methoxy-quinazoline, 4-[(3-chloro-4-fluorophenyl)amino]-6-[2-(6,6-dimethyl-2-oxo-morpholin-4-yl)-ethoxy]-7-cyclopentyloxy-quinazoline, 4-[(3-chloro-4-fluorophenyl)amino]-6-[3-(6,6-dimethyl-2-oxo-morpholin-4-yl)-propyloxy]-7-cyclopentyloxy-quinazoline and (R)-4-[(1-phenyl-ethyl)amino]-6-[3-(6,6-dimethyl-2-oxo-morpholin-4-yl)-propyloxy]-7-cyclopentyloxy-quinazoline are excluded, the tautomers, the stereoisomers and the salts thereof.

Most particularly preferred compounds of general formula I are also those wherein $R_a$ denotes a 3-chloro-4-fluorophenyl group, $R_b$ denotes a cyclopentyloxy, cyclopropylmethoxy, cyclopentylmethoxy, tetrahydrofuran-3-yloxy or tetrahydrofuranylmethoxy group and $R_c$ denotes a $R_3$—$(CH_2)_m$—O group, wherein
$R_3$ denotes a 2-oxo-morpholin-4-yl group substituted by one or two methyl groups and
m denotes the number 2, with the proviso that the compounds 4-[(3-chloro-4-fluorophenyl)amino]-6-cyclopentyloxy-7-[2-(6,6-dimethyl-2-oxo-morpholin-4-yl)-ethoxy]-quinazoline, 4-[(3-chloro-4-fluorophenyl)amino]-7-[2-(6,6-dimethyl-2-oxo-morpholin-4-yl)-ethoxy]-6-cyclopentyloxy-quinazoline, 4-[(3-chloro-4-fluorophenyl)amino]-7-[2-(6,6-dimethyl-2-oxo-morpholin-4-yl)-ethoxy]-6-cyclopropylmethoxy-quinazoline and 4-[(3-chloro-4-fluorophenyl)amino]-7-[2-(6,6-dimethyl-2-oxo-morpholin-4-yl)-ethoxy]-6-cyclopentylmethoxy-quinazoline, are excluded, the tautomers, the stereoisomers and the salts thereof.

The following are mentioned by way of example as most particularly preferred compounds:

(1) 4-[(3-chloro-4-fluorophenyl)amino]-6-cyclopentylmethoxy-7-[2-(6,6-dimethyl-2-oxo-morpholin-4-yl)-ethoxy]-quinazoline, (2) 4-[(3-chloro-4-fluorophenyl)amino]-6-cyclopentyloxy-7-{2-[N-(2-oxo-tetrahydrofuran-4-yl)-N-methyl-amino]-ethoxy}-quinazoline, (3) 4-[(3-chloro-4-fluorophenyl)amino]-6-cyclopropylmethoxy-7-[2-(6,6-dimethyl-2-oxo-morpholin-4-yl)-ethoxy]-quinazoline, (4) 4-[(3-chloro-4-fluorophenyl)amino1-7-cyclobutyloxy-6-[3-(6,6-dimethyl-2-oxo-morpholin-4-yl)-propyloxy]-quinazoline, (5) 4-(3-chloro-4-fluorophenyl)amino]-7-cyclopropylmethoxy-6-[3-(6,6-dimethyl-2-oxo-morpholin-4-yl)-propyloxy]-quinazoline, (6) 4-[(3-chloro-4-fluorophenyl)amino]-6-cyclopropylmethoxy-7-{2-[N-(2-oxo-tetrahydrofuran-4-yl)-N-methyl-amino]-ethoxy}-quinazoline, (7) 4-[(3-bromo-phenyl)amino]-6-[2-((S)-6-methyl-2-oxo-morpholin-4-yl)-ethoxy]-7-methoxy-quinazoline, (8) 4-[(3-bromo-phenyl)amino]-6-[2-((R)-6-methyl-2-oxo-morpholin-4-yl)-ethoxy]-7-methoxy-quinazoline, (9) 4-[(3-chloro-4-fluorophenyl)amino]-6-[2-((R)-6-methyl-2-oxo-morpholin-4-yl)-ethoxy]-7-methoxy-quinazoline,

(10) 4-[(3-chloro-4-fluorophenyl)amino]-6-[3-((R)-6-methyl-2-oxo-morpholin-4-yl)-propyloxy]-7-methoxy-quinazoline,

(11) 4-[(R)-(1-phenyl-ethyl)amino]-6-[3-((S)-6-methyl-2-oxo-morpholin-4-yl)-propyloxy]-7-methoxy-quinazoline,

(12) 4-[(R)-(1-phenyl-ethyl)amino]-6-[2-((S)-6-methyl-2-oxo-morpholin-4-yl)-ethoxy]-7-ethoxy-quinazoline and

(13) 4-[(3-chloro-4-fluorophenyl)amino]-6-[2-((S)-6-methyl-2-oxo-morpholin-4-yl)-ethoxy]-7-methoxy-quinazoline, the tautomers, the stereoisomers and the salts thereof.

The compounds of general formula I may be prepared by the following methods, for example:

a) reacting a compound of general formula

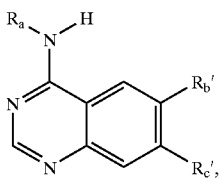

(II)

wherein
R$_a$ is as hereinbefore defined,
one of the groups R$_b$' or R$_c$' represents a methoxy, cyclobutyloxy, cyclopentyloxy, cyclopropylmethoxy, cyclobutylmethoxy or cyclopentylmethoxy group and the other group R$_b$' or R$_c$' represents a Z$_1$—(CH$_2$)$_m$—O group, wherein
m is as hereinbefore defined and
Z$_1$ denotes a leaving group such as a halogen atom or a sulphonyloxy group such as a chlorine or bromine atom, a methanesulphonyloxy or p-toluenesulphonyloxy group,
with a compound of general formula

 ,(III)

wherein
R$_3$ is as hereinbefore defined.

The reaction is optionally carried out in a solvent or mixture of solvents such as methylene chloride, acetonitrile, dimethylformamide, dimethylsulphoxide, sulpholane, benzene, toluene, chlorobenzene, tetrahydrofuran, benzene/tetrahydrofuran or dioxan, conveniently in the presence of a tertiary organic base such as triethylamine or N-ethyl-diisopropylamine, whilst these organic bases may simultaneously also act as solvent, or in the presence of an inorganic base such as sodium carbonate or potassium carbonate, expediently at temperatures between −20 and 200° C., preferably at temperatures between 0 and 150° C.

b) cyclising a compound of general formula

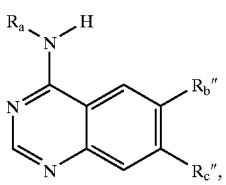

(IV)

optionally formed in the reaction mixture
wherein
R$_a$ is as hereinbefore defined,
one of the groups R$_b$" or R$_c$" represents a methoxy, cyclobutyloxy, cyclopentyloxy, cyclopropylmethoxy, cyclobutylmethoxy or cyclopentylmethoxy group and the other group R$_b$" or R$_c$" represents a R$_3$'—(CH$_2$)$_m$—O group, wherein
m is as hereinbefore defined and
R$_3$' denotes a R$_4$—O—CO—CH$_2$—N—CH$_2$CH$_2$—OH group substituted at the methylene groups by one or two methyl or ethyl groups, wherein
R$_4$ represents a hydrogen atom or a C1-4-alkyl group.

The reaction is optionally carried out in a solvent or mixture of solvents such as methylene chloride, acetonitrile, dimethylformamide, dimethyl sulphoxide, sulpholane, benzene, toluene, chlorobenzene, tetrahydrofuran, benzene/tetrahydrofuran or dioxan, expediently in the presence of an anhydrous acid such as trifluoroacetic acid, methanesulphonic acid or sulphuric acid or in the presence of a dehydrating agent, e.g. in the presence of isobutyl chloroformate, thionyl chloride, trimethylchlorosilane, phosphorus trichloride, phosphorus pentoxide, N,N'-dicyclohexylcarbodiimide, N,N'-dicyclohexyl-carbodiimide/N-hydroxysuccinimide or 1-hydroxy-benzotriazole, N,N'-carbonyldiimidazole or triphenylphosphine/carbon tetrachloride, at temperatures between −20 and 200° C., but preferably at temperatures between −10 and 160° C.

In the reactions described hereinbefore, any reactive groups present such as hydroxy, carboxy or imino groups may be protected during the reaction by conventional protecting groups which are cleaved again after the reaction.

For example, a protecting group for a hydroxy group may be a trimethylsilyl, acetyl, benzoyl, methyl, ethyl, tert.butyl, trityl, benzyl or tetrahydropyranyl group, protecting groups for a carboxy group may be a trimethylsilyl, methyl, ethyl, tert.butyl, benzyl or tetrahydropyranyl group, and protecting groups for an imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group.

Any protecting group used is optionally subsequently cleaved for example by hydrolysis in an aqueous solvent, e.g. in water, isopropanol/water, acetic acid/water, tetrahydrofuran/water or dioxan/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxan, methanol or diethyl ether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

In addition, if the new compounds of formula I thus obtained contain a carboxy, hydroxyphosphoryl, sulpho or 5-tetrazolyl group, they may, if desired, subsequently be converted into the salts thereof with inorganic or organic bases, particularly for pharmaceutical use, into the physiologically acceptable salts thereof. Suitable bases for this purpose include, for example, sodium hydroxide, potassium hydroxide, arginine, cyclohexylamine, ethanolamine, diethanolamine and triethanolamine.

The compounds of general formulae II to IV used as starting materials are known from the literature in some cases or may be obtained by methods known from the literature (cf. Examples I to XIV).

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosine kinase itself. It is also possible that the transmission of signals to components located further down is blocked.

The biological properties of the new compounds were investigated as follows:

The inhibition of the EGF-R-mediated signal transmission can be demonstrated e.g. with cells which express human EGF-R and whose survival and proliferation depend on stimulation by EGF or TGF-alpha. A cell line of murine origin dependent on interleukin-3-(IL-3) which was genetically modified to express functional human EGF-R was used here. The proliferation of these cells known as F/L-HERc can therefore be stimulated either by murine IL-3 or by EGF (cf. von Rüden, T. et al. in EMBO J. 7, 2749–2756 (1988) and Pierce, J. H. et al. in Science 239, 628–631 (1988)).

The starting material used for the F/L-HERc cells was the cell line $FDC-P_1$, the production of which has been described by Dexter, T. M. et al. in J. Exp. Med. 152, 1036–1047 (1980). Alternatively, however, other growth-factor-dependent cells may also be used (cf. for example Pierce, J. H. et al. in Science 239, 628–631 (1988), Shibuya, H. et al. in Cell 70, 57–67 (1992) and Alexander, W. S. et al. in EMBO J. 10, 3683–3691 (1991)). For expressing the human EGF-R cDNA (cf. Ullrich, A. et al. in Nature 309, 418–425 (1984)) recombinant retroviruses were used as described by von Rüden, T. et al., EMBO J. 7, 2749–2756 (1988), except that the retroviral vector LXSN (cf. Miller, A. D. et al. in BioTechniques 7, 980–990 (1989)) was used for the expression of the EGF-R cDNA and the line GP+E86 (cf. Markowitz, D. et al. in J. Virol. 62, 1120–1124 (1988)) was used as the packaging cell.

The test was performed as follows:

F/L-HERc cells were cultivated in RPMI/1640 medium (BioWhittaker), supplemented with 10% foetal calf serum (FCS, Boehringer Mannheim), 2 mM glutamine (BioWhittaker), standard antibiotics and 20 ng/ml of human EGF (Promega), at 37° C. and 5% $CO_2$. In order to investigate the inhibitory activity of the compounds according to the invention, 1.5×104 cells per well were cultivated in triplicate in 96-well dishes in the above medium (200 μl), the cell proliferation being stimulated with either EGF (20 ng/ml) or murine IL-3. The IL-3 used was obtained from culture supernatants of the cell line X63/0 mIL-3 (cf. Karasuyama, H. et al. in Eur. J. Immunol. 18, 97–104 (1988)). The compounds according to the invention were dissolved in 100% dimethylsulphoxide (DMSO) and added to the cultures in various dilutions, the maximum DMSO concentration being 1%. The cultures were incubated for 48 hours at 37° C.

In order to determine the inhibitory activity of the compounds according to the invention the relative cell number was measured in O.D. units using the Cell Titer $_{96}$™ AQueous Non-Radioactive Cell Proliferation Assay (Promega). The relative cell number was calculated as a percentage of the control (F/LHERc cells without inhibitor) and the concentration of active substance which inhibits the proliferation of the cells by 50% ($IC_{50}$) was derived therefrom. The following results were obtained:

| Compound (Example No.) | Inhibition of EGF-dependent proliferation $IC_{50}$ [nM] |
| --- | --- |
| 1 | 59 |
| 1(1) | 29 |
| 1(2) | 29 |
| 2(1) | 36 |

The compounds of general formula I according to the invention thus inhibit signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation by tyrosine kinases, e.g. in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas and protein loss syndrome, and also for treating nasal polyps and polyps of the gastrointestinal tract of various origins such as villous or adenomatous polyps of the large intestine, but also polyps in familial polyposis coli, in intestinal polyps in Gardner's syndrome, in polyps throughout the entire gastro-intestinal tract in Peutz-Jeghers Syndrome, in inflammatory pseudopolyps, in juvenile polyps, in colitis cystica profunda and in pneumatosis cystoides intestinales.

In addition, the compounds of general formula I and the physiologically acceptable salts thereof may be used to treat kidney diseases, particularly in cystic changes as in cystic kidneys, for treating renal cysts which may be idiopathic in origin or occur in syndromes such as tubercular sclerosis, in von Hippel-Lindau syndrome, in nephrophthisis and spongy kidney and other diseases caused by abnormal function of tyrosine kinases, such as e.g. epidermal hyperproliferation (psoriasis), inflammatory processes, diseases of the immune system, hyperproliferation of haematopoietic cells, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. For treating respiratory tract diseases, these compounds may be used on their own or in conjunction with other therapeutic agents for the airways, such as substances with a secretolytic, broncholytic and/or anti-inflammatory activity. For treating diseases in the region of the gastrointestinal tract, these compounds may also be administered on their own or in conjunction with substances having an effect on motility or secretion, or anti-inflammatory substances. These combinations may be administered either simultaneously or sequentially.

These compounds may be administered either on their own or in conjunction with other active substances by intravenous, subcutaneous, intramuscular, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:

Preparation of the starting compounds:

EXAMPLE I

4-[(3-Chloro-4-fluorophenyl)amino]-6-cyclopentylmethoxy-7-(2-bromo-ethoxy)-quinazoline 4.84 g potassium carbonate are added to 3.50 g of 4-[(3-chloro-4-fluorophenyl)amino]-6-cyclopentylmethoxy-7-hydroxy-quinazoline and 6.89 ml of 1,2-dibromoethane in 40 ml of N,N-dimethylformamide. The reaction mixture is stirred for 1.5 hours at 80° C. under a nitrogen atmosphere. After cooling to ambient temperature the reaction mixture is filtered and the filtrate is evaporated down in vacuo. The oily brown residue is cooled in an ice bath and triturated with a little methanol, whereupon a yellowish solid crystallises out. The precipitate is suction filtered, washed with cold methanol and dried in the vacuum desiccator.

Yield: 2.60 g (58% of theory), $R_f$ value: 0.82 (silica gel, methylene chloride/methanol 9:1) Mass spectrum (ESI$^+$): m/z=494, 496, 498 [M+H]$^+$.

The following compounds are obtained analogously to Example I:

(1) 4-[(3-Chloro-4-fluorophenyl)amino]-6-cyclopropylmethoxy-7-(2-bromoethoxy)-quinazoline (The Reaction is Carried out in Acetonitrile as Solvent)

$R_f$ value: 0.72 (silica gel, methylene chloride/methanol/concentrated, aqueous ammonia solution=90:10:0.1); Mass spectrum (ESI$^-$): m/z=464, 466, 468 [M-H]$^{31}$.

(2) 4-[(3-Chloro-4-fluorophenyl)amino]-6-cyclopentyloxy-7-(2-bromoethoxy)-quinazoline $R_f$ value: 0.65 (silica gel, methylene chloride/methanol/concentrated, aqueous ammonia solution=90:10:0.1); Mass spectrum (ESI$^-$): m/z=478, 480, 482 [M-H]$^-$.

(3) 4-[(3-Chloro-4-fluorophenyl)amino]-7-cyclobutyloxy-6-(3-bromopropyloxy)-quinazoline (The Reaction is Carried out in Acetonitrile as Solvent)

$R_f$ value: 0.62 (silica gel, methylene chloride/methanol 9:1); Mass spectrum (ESI$^-$): m/z=478, 480, 482 [M-H]$^-$.

(4) 4-[(3-Chloro-4-fluorophenyl)amino]-7-cyclopropylmethoxy-6-(3-bromopropyloxy)-quinazoline (The Reaction is Carried out in Acetonitrile as Solvent)

$R_f$ value: 0.74 (silica gel, methylene chloride/methanol 9:1); Mass spectrum (ESI$^-$): m/z=478, 480, 482 [M-H]$^-$.

(5) 4-[(3-Bromo-phenyl)amino]-6-(2-bromoethoxy)-7-methoxy-quinazoline

Melting point: 244° C.; Mass spectrum (ESI+): m/z=452, 454, 456 [M+H]$^+$.

(6) 4-[(R)-(1-Phenyl-ethyl)amino]-6-(3-bromopropyloxy)-7-methoxy-quinazoline (The Reaction is Carried out with Potassium tert.Butoxide as Base)

$R_f$ value: 0.60 (silica gel, ethyl acetate/methanol 9:1).

(7) 4-[(R)-(1-Phenyl-ethyl)amino]-6-(2-bromoethoxy)-7-methoxy-quinazoline (The Reaction is Carried out with Potassium tert.Butoxide as Base)

Melting point: 255° C.; Mass spectrum (ESI$^+$): m/z=402, 404 [M+H]$^+$.

(8) 4-[(3-Chloro-4-fluorophenyl)amino]-6-(3-hydroxy-propyloxy)-7-cyclobutyloxy-quinazoline $R_f$ value: 0.50 (silica gel, methylene chloride/methanol= 90:10); Mass spectrum (ESI$^+$): m/z=418, 420 [M+H]$^+$.

(9) 4-[(3-Chloro-4-fluorophenyl)amino]-6-(3-hydroxy-propyloxy)-7-cyclopropylmethoxy-quinazoline $R_f$ value: 0.21 (silica gel, methylene chloride/methanol=95:5); Mass spectrum (ESI$^+$): m/z=418, 420 [M+H]$^+$.
(10) 4-[(3-Chloro-4-fluorophenyl)amino]-6-(2-bromo-ethoxy)-7-cyclopentyloxy-quinazoline $R_f$ value: 0.67 (silica gel, methylene chloride/methanol=90:10); Mass spectrum (ESI$^+$): m/z=480, 482, 484 [M+H]$^+$.
(11) 4-[(3-Chloro-4-fluorophenyl)amino]-6-(2-bromo-ethoxy)-7-cyclopropylmethoxy-quinazoline $R_f$ value: 0.68 (silica gel, methylene chloride/methanol=90:10); Mass spectrum (ESI$^+$): m/z=466, 468, 470 [M+H]$^+$.
(12) 4-[(3-Chloro-4-fluorophenyl)amino]-6-cyclopropylmethoxy-7-(3-hydroxy-propyloxy)-quinazoline $R_f$ value: 0.53 (silica gel, methylene chloride/methanol=90:10); Mass spectrum (ESI$^+$): m/z=418, 420 [M+H]$^+$.
(13) 4-[(3-Chloro-4-fluorophenyl)amino]-6-(4-hydroxy-butyloxy)-7-cyclopentyloxy-quinazoline $R_f$ value: 0.46 (silica gel, ethyl acetate).
(14) 4-[(3-Chloro-4-fluorophenyl)amino]-6-(2-bromo-ethoxy)-7-((R)-tetrahydrofuran-3-yloxy)-quinazoline $R_f$ value: 0.37 (silica gel, methylene chloride/methanol=9:1); Mass spectrum (ESI$^-$): m/z=480, 482, 484 [M−H]$^-$.
(15) 4-[(3-Chloro-4-fluorophenyl)amino]-6-(2-bromo-ethoxy)-7-[(R)-(tetrahydrofuran-2-yl)methoxy]-quinazoline Mass spectrum (ESI$^-$): m/z=494, 496, 498 [M−H]$^-$;
(16) 4-[(3-Chloro-4-fluorophenyl)amino]-7-(2-bromo-ethoxy)-6-[(S)-(tetrahydrofuran-2-yl)methoxy]-quinazoline;

Mass spectrum (ESI$^-$): m/z=494, 496, 498 [M−H]$^-$.

EXAMPLE II

4-[(3-Chloro-4-fluorophenyl)amino]-6-cyclopentylmethoxy-7-hydroxy-quinazoline 4.99 g of 4-[(3-chloro-4-fluorophenyl)amino]-6-cyclopentylmethoxy-7-methylcarbonyloxy-quinazoline are suspended in 80 ml of methanol and 1.80 ml of concentrated, aqueous ammonia solution are added. The reaction mixture is stirred overnight at ambient temperature. For working up the reaction mixture is diluted with 500 ml methylene chloride, washed with water and saturated sodium chloride solution, dried over magnesium sulphate and concentrated by evaporation. 4.30 g of a brownish solid are obtained. The crude product is stirred with tert.butyl methyl ether, suction filtered, washed with a little tert.butyl methyl ether and dried in vacuo at ambient temperature.

Yield: 3.59 g (80% of theory), $R_f$ value: 0.48 (silica gel, methylene chloride/methanol/concentrated, aqueous ammonia solution=90:10:0.1); Mass spectrum (ESI$^+$): m/z=388, 340 [M+H]$^+$.

The following compounds are obtained analogously to Example II:
(1) 4-[(3-Chloro-4-fluorophenyl)amino]-6-cyclopropylmethoxy-7-hydroxy-quinazoline $R_f$ value: 0.56 (silica gel, methylene chloride/methanol 9:1); Mass spectrum (ESI$^-$): m/z=358, 360 [M−H]$^-$.
(2) 4-[(3-Chloro-4-fluorophenyl)amino]-6-cyclopentyloxy-7-hydroxy-quinazoline $R_f$ value: 0.53 (silica gel, methylene chloride/methanol/concentrated, aqueous ammonia solution=90:10:0.1); Mass spectrum (ESI$^+$): m/z=374, 376 [M+H]$^+$.
(3) 6-Benzyloxy-4-[(3-chloro-4-fluorophenyl)amino]-7-hydroxy-quinazoline $R_f$ value: 0.54 (silica gel, methylene chloride/methanol/concentrated, aqueous ammonia solution=90:10:0.1); Mass spectrum (ESI$^+$): m/z=396, 398 [M+H]$^+$.
(4) 4-[(3-Bromo-phenyl)amino]-6-hydroxy-7-methoxy-quinazoline (The Reaction is Carried out with Sodium Hydroxide Solution in Ethanol as Solvent)

$R_f$ value: 0.23 (silica gel, ethyl acetate); Mass spectrum (ESI$^+$): m/z=346, 348 [M+H]$^+$.
(5) 4-[(3-Chloro-4-fluorophenyl)amino]-7-hydroxy-6-((S)-tetrahydrofuran-3-yloxy)-quinazoline $R_f$ value: 0.57 (silica gel, methylene chloride/methanol=9:1); Mass spectrum (ESI$^+$): m/z=376, 378 [M+H]$^+$.
(6) 4-[(3-Chloro-4-fluorophenyl)amino]-7-hydroxy-6-[(S)-(tetrahydrofuran-2-yl)methoxy]-quinazoline $R_f$ value: 0.42 (silica gel, methylene chloride/methanol=9:1).

EXAMPLE III

4-[(3-Chloro-4-fluorophenyl)amino]-6-cyclopentylmethoxy-7-methylcarbonyloxy-quinazoline 4.03 g of 4-chloro-6-cyclopentylmethoxy-7-methylcarbonyloxy-quinazoline are suspended in 70 ml of isopropanol and 1.95 g of 3-chloro-4-fluoro-aniline are added. The reaction mixture is refluxed for two hours under a nitrogen atmosphere. After cooling to ambient temperature the light-coloured precipitate formed is suction filtered, washed with a little isopropanol and dried in the air.

Yield: 4.99 g (92% of theory), $R_f$ value: 0.80 (silica gel, methylene chloride/methanol/concentrated, aqueous ammonia solution=90:10:0.1); Mass spectrum (ESI$^+$): m/z=430, 432 [M+H]$^+$.

The following compounds are obtained analogously to Example II:
(1) 4-[(3-Chloro-4-fluorophenyl)amino]-6-cyclopropylmethoxy-7-methylcarbonyloxy-quinazoline $R_f$ value: 0.86 (silica gel, methylene chloride/methanol=9:1); Mass spectrum (ESI$^+$): m/z=402, 404 [M+H]$^+$.
(2) 4-[(3-Chloro-4-fluorophenyl)amino]-6-cyclopentyloxy-7-methylcarbonyloxy-quinazoline $R_f$ value: 0.73 (silica gel, methylene chloride/methanol/concentrated, aqueous ammonia solution=90:10:0.1); Mass spectrum (ESI$^+$): m/z=416, 418 [M+H]$^+$.
(3) 6-Benzyloxy-4-[(3-chloro-4-fluorophenyl)amino]-7-methylcarbonyloxy-quinazoline $R_f$ value: 0.76 (silica gel, methylene chloride/methanol/concentrated, aqueous ammonia solution=90:10:0.1); Mass spectrum (ESI$^+$): m/z=438, 440 [M+H]$^+$.
(4) 4-[(3-Bromo-phenyl)amino]-6-methylcarbonyloxy-7-methoxy-quinazoline $R_f$ value: 0.50 (silica gel, ethyl acetate); Mass spectrum (ESI$^+$): m/z=388, 390 [M+H]$^+$.
(5) 4-[(R)-(1-Phenyl-ethyl)amino]-6-hydroxy-7-methoxy-quinazoline (The Acetoxy Protecting Group has Already been Cleaved under the Reaction Conditions)

$R^f$ value: 0.46 (silica gel, ethyl acetate); Mass spectrum (ESI$^+$): m/z=296 [M+H]$^+$.
(6) 6-Benzyloxy-4-[(3-chloro-4-fluorophenyl)amino]-7-cyclopentyloxy-quinazoline (Pyridine is Added as Auxiliary Base)

$R_f$ value: 0.51 (silica gel, methylene chloride/methanol=95:5); Mass spectrum (ESI$^+$): m/z=464, 466 [M+H]$^+$.
(7) 4-[(3-Chloro-4-fluorophenyl)amino]-7-methylcarbonyloxy-6-((S)-tetrahydrofuran-3-yloxy)-quinazoline $R_f$ value: 0.67 (silica gel, methylene chloride/methanol=9:1); Mass spectrum (ESI$^-$): m/z=416, 418 [M−H]$^-$.
(8) 4-[(3-Chloro-4-fluorophenyl)amino]-7-methylcarbonyloxy-6-[(S)-(tetrahydrofuran-2-yl)methoxy]-quinazoline-hydrochloride Melting point: 274–276° C.; Mass spectrum (ESI$^+$): m/z=432, 434 [M+H]$^+$.

EXAMPLE IV

4-Chloro-6-cyclopentylmethoxy-7-methylcarbonyloxy-quinazoline 3.80 g of 4-hydroxy-6-cyclopentylmethoxy-7-methylcarbonyloxy-quinazoline are suspended in 90 ml thionyl chloride and heated to boiling under a nitrogen atmosphere. After the addition of four drops of N,N-dimethylformamide the reaction mixture is refluxed for a further two hours. After cooling to ambient temperature the excess thionyl chloride is distilled off in a water jet vacuum. The brown residue is stirred with 30 ml toluene. The solvent is distilled off, leaving 4.30 g of a greyish-brown solid, which is reacted further without any more purification.

$R_f$ value: 0.89 (silica gel, methylene chloride/methanol/concentrated, aqueous ammonia solution=90:10:0.1).

The following compounds are obtained analogously to Example IV:
(1) 4-Chloro-6-cyclopropylmethoxy-7-methylcarbonyloxy-quinazoline $R_f$ value: 0. 84 (silica gel, methylene chloride/methanol=9:1).
(2) 4-Chloro-6-cyclopentyloxy-7-methylcarbonyloxy-quinazoline $R_f$ value: 0.69 (silica gel, methylene chloride/methanol/concentrated, aqueous ammonia solution=90:10:0.1).
(3) 6-Benzyloxy4-chloro-7-methylcarbonyloxy-quinazoline $R_f$ value: 0.77 (silica gel, methylene chloride/methanol/concentrated, aqueous ammonia solution=90:10:0.1).
(4) 6-Benzyloxy4-chloro-7-cyclopentyloxy-quinazoline $R_f$ value: 0.91 (silica gel, methylene chloride/methanol=9:1).
(5) 4-Chloro-7-methylcarbonyloxy-6-((S)-tetrahydrofuran-3-yloxy)-quinazoline $R_f$ value: 0.83 (silica gel, ethyl acetate/methanol=9:1).
(6) 4-Chloro-7-methylcarbonyloxy-6-[(S)-(tetrahydrofuran-2-yl)methoxy]-quinazoline $R_f$ value: 0.48 (silica gel, cyclohexane/ethyl acetate=1:1).

EXAMPLE V

4-Hydroxy-6-cyclopentylmethoxy-7-methylcarbonyloxy-quinazoline 4.30 g of 4,7-dihydroxy-6-cyclopentylmethoxy-quinazoline in 100 ml of pyridine are heated to 80° C. under a nitrogen atmosphere. 1.80 ml of acetic anhydride are added to the dark-brown suspension. The reaction mixture is stirred for three hours at 80° C., during which time a total solution is formed. After cooling to ambient temperature the reaction mixture is poured onto about 800 ml of ice water. The precipitate formed is suction filtered and washed thoroughly with water. The light-grey solid is dried in the vacuum desiccator.

Yield: 3.82 g of (77% of theory), $R_f$ value: 0.49 (silica gel, methylene chloride/methanol=9:1); Mass spectrum (ESI$^-$): m/z=301 [M–H]$^{31}$ .

The following compounds are obtained analogously to Example V:
(1) 4-Hydroxy-6-cyclopropylmethoxy-7-methylcarbonyloxy-quinazoline $R_f$ value: 0.53 (silica gel, methylene chloride/methanol=9:1); Mass spectrum (ESI$^-$): m/z=273 [M–H]$^-$.
(2) 4-Hydroxy-6-cyclopentyloxy-7-methylcarbonyloxy-quinazoline Melting point: 209–212° C.; Mass spectrum (ESI$^-$): m/z=287 [M–H]$^-$.
(3) 6-Benzyloxy4-hydroxy-7-methylcarbonyloxy-quinazoline $R_f$ value: 0.48 (silica gel, methylene chloride/methanol/concentrated, aqueous ammonia solution=90:10:0.1); Mass spectrum (ESI$^-$): m/z=309 [M–H]$^-$.
(4) 4-Hydroxy-7-methylcarbonyloxy-6-((S)-tetrahydrofuran-3-yloxy)-quinazoline $R_f$ value: 0.62 (Reversed Phase ready-made TLC plate (E. Merck), acetonitrile/water/trifluoroacetic acid=50:50:1); Mass spectrum (ESI$^+$): m/z=291 [M+H]$^+$.
(5) 4-Hydroxy-7-methylcarbonyloxy-6-[(S)-(tetrahydrofuran-2-yl)methoxy]-quinazoline $R_f$ value: 0.50 (silica gel, methylene chloride/methanol=9:1); Mass spectrum (ESI$^+$): m/z=305 [M+H]$^+$.

EXAMPLE VI

4,7-Dihydroxy-6-cyclopentylmethoxy-quinazoline 5.76 g of 2-amino-5-cyclopentylmethoxy-4-hydroxy-benzoic acid and 6.52 g of formamidine acetate in 140 ml ethanol are refluxed for about three hours. For working up the reaction mixture is evaporated down to about 100 ml and 300 ml of ice water are added, whereupon a grey precipitate is formed. The precipitate is suction filtered, washed with water and dried in the vacuum desiccator.

Yield: 4.57 g of (77% of theory), $R_f$ value: 0.25 (silica gel, methylene chloride/methanol=95:5); Mass spectrum (ESI): m/z=259 [M–H]$^-$.

The following compounds are obtained analogously to Example VI:
(1) 4,7-Dihydroxy-6-cyclopropylmethoxy-quinazoline $R_f$ value: 0.45 (silica gel, methylene chloride/methanol/concentrated aqueous ammonia solution=90:10:0.1); Mass spectrum (ESI$^-$): m/z=231 [M–H]$^-$.
(2) 4,7-Dihydroxy-6-cyclopentyloxy-quinazoline $R_f$ value: 0.42 (silica gel, methylene chloride/methanol/concentrated aqueous ammonia solution=90:10:0.1); Mass spectrum (El): m/z=246 [M]$^+$.
(3) 6-Benzyloxy-4,7-dihydroxy-quinazoline $R_f$ value: 0.44 (silica gel, methylene chloride/methanol/concentrated aqueous ammonia solution=90:10:0.1); Mass spectrum (ESI$^-$): m/z=267 [M–H]$^-$.
(4) 6-Benzyloxy-7-cyclopentyloxy4-hydroxy-quinazoline Melting point: 221–223° C.; Mass spectrum (ESI$^+$): m/z=337 [M+H]$^+$.
(5) 4,7-Dihydroxy-6-((S)-tetrahydrofuran-3-yloxy)-quinazoline $R_f$ value: 0.69 (Reversed Phase ready-made TLC plate (E. Merck), acetonitrile/water/trifluoroacetic acid=50:50:1); Mass spectrum (ESI$^-$): m/z=247 [M–H]$^-$.
(6) 4,7-Dihydroxy-6-[(S)-(tetrahydrofuran-2-yl)methoxy]-quinazoline $R_f$ value: 0.56 (silica gel, methylene chloride/methanol=9:1); Mass spectrum (ESI$^-$): m/z=261 [M–H]$^-$.

EXAMPLE VII

2-Amino-5-cyclopentylmethoxy-4-hydroxy-benzoic Acid 6.50 g of 5-cyclopentylmethoxy4-hydroxy-2-nitro-benzoic acid are dissolved in 130 ml of methanol, 2.00 g of Raney nickel are added and the mixture is hydrogenated for about three hours under a hydrogen pressure of 50 psi at roughly ambient temperature until the calculated amount of hydrogen has been taken up. The catalyst is filtered off and washed with hot methanol. The filtrate is evaporated down in vacuo. A brownish solid remains, which is reacted further without any more purification.

Yield: 5.79 g of (100% of theory), $R_f$ value: 0.67 (silica gel, methylene chloride/methanol=9:1); Mass spectrum (ESI⁻): m/z=250 [M−H]⁻.

The following compounds are obtained analogously to Example VII:

(1) 2-Amino-5-cyclopropylmethoxy4-hydroxy-benzoic Acid $R_f$ value: 0.51 (silica gel, methylene chloride/methanol/concentrated aqueous ammonia solution=90:10:0.1); Mass spectrum (ESI⁻): m/z=222 [M−H]⁻.

(2) 2-Amino-5-cyclopentyloxy4-hydroxy-benzoic Acid $R_f$ value: 0.38 (silica gel, methylene chloride/methanol/concentrated aqueous ammonia solution=90:10:0.1); Mass spectrum (ESI⁺): m/z=238 [M+H]⁺.

(3) 2-Amino-5-benzyloxy4-hydroxy-benzoic acid $R_f$ value: 0.52 (silica gel, methylene chloride/methanol/concentrated aqueous ammonia solution=90:10:0.1); Mass spectrum (ESI⁻): m/z=258 [M−H]⁻.

(4) Cyclopentyl 2-Amino-5-benzyloxy4-cyclopentyloxy-benzoate (The Reaction is Carried out in a 1:1 Mixture of Methanol and Tetrahydrofuran)

$R_f$ value: 0.84 (silica gel, ethyl acetate/cyclohexane=1:1); Mass spectrum (ESI⁺): m/z=396 [M+H]⁺.

(5) 2-Amino-4-hydroxy-5-((S)-tetrahydrofuran-3-yloxy)-benzoic Acid $R_f$ value: 0.70 (Reversed Phase ready-made TLC plate (E. Merck), acetonitrile/water/trifluoroacetic acid=50:50:1); Mass spectrum (ESI⁻): m/z=238 [M−H]⁻.

(6) 2-Amino-4-hydroxy-5-[(S)-(tetrahydrofuran-2-yl)methoxy]-benzoic Acid $R_f$ value: 0.59 (Reversed Phase ready-made TLC plate (E. Merck), acetonitrile/water/trifluoroacetic acid=50:50:1); Mass spectrum (ESI⁻): m/z=252 [M−H]⁻.

EXAMPLE VIII

5-Cyclopentylmethoxy-4-hydroxy-2-nitro-benzoic Acid 15.37 g of 4,5-methylendioxy-2-nitro-benzoic acid and 51.84 ml of cyclopentylmethanol are dissolved in 100 ml dimethyl sulphoxide and cooled in an ice bath under a nitrogen atmosphere. Then 3.90 g of sodium are added in batches. The reaction mixture is stirred for 30 minutes while cooling with an ice bath, then briefly heated to 3540° C. and subsequently stirred for a further three hours while cooling with an ice bath. Then the ice bath is removed and the reaction mixture is stirred overnight at ambient temperature. The reddish-dark brown reaction solution is poured onto about 800 ml of acetone, whereupon a dark brown precipitate is formed. The precipitate is suction filtered, washed with acetone, dissolved in 300–400 ml water and adjusted to about pH 2 with 60 ml of 2N hydrochloric acid. The aqueous solution is extracted several times with methylene chloride. The combined extracts are washed with saturated sodium chloride solution, dried over sodium sulphate and concentrated by evaporation. The dark-brown oily flask residue is dissolved in 800 ml of methylene chloride and purified through a silica gel charge with methylene chloride/methanol (9:1). A brown oil is obtained which is crystallised by stirring with water while cooling with an ice bath. The brownish precipitate formed is suction filtered, washed with a little water and dried in the vacuum desiccator.

Yield: 9.55 g of (47% of theory), $R_f$ value: 0.67 (silica gel, toluene/dioxan/ethanol/glacial acetic acid=90:10:10:6); Mass spectrum (ESI⁻): m/z=280 [M−H]⁻.

The following compounds are obtained analogously to Example VIII:

(1) 5-Cyclopropylmethoxy4-hydroxy-2-nitro-benzoic Acid $R_f$ value: 0.61 (silica gel, toluene/dioxan/ethanol/glacial acetic acid=90:10:10:6); Mass spectrum (ESI⁻): m/z=252 [M−H]⁻.

(2) 5-Cyclopentyloxy-4-hydroxy-2-nitro-benzoic Acid $R_f$ value: 0.62 (silica gel, toluene/dioxan/ethanol/glacial acetic acid=90:10:10:6); Mass spectrum (ESI⁻): m/z=266 [M−H]⁻.

(3) 5-Benzyloxy-4-hydroxy-2-nitro-benzoic Acid

Melting point: 176–178° C.; Mass spectrum (ESI⁻): m/z=288 [M−H]⁻.

(4) 4-Hydroxy-2-nitro-5-((S)-tetrahydrofuran-3-yloxy)-benzoic Acid $R_f$ value: 0.58 (Reversed Phase ready-made TLC plate (E. Merck), acetonitrile/water/trifluoroacetic acid=50:50:1); Mass spectrum (ESI⁻): m/z=268 [M−H]⁻.

(5) 4-Hydroxy-2-nitro-5-[(S)-(tetrahydrofuran-2-yl)methoxy]-benzoic Acid $R_f$ value: 0.53 (Reversed Phase ready-made TLC plate (E. Merck), acetonitrile/water/trifluoroacetic acid=50:50:1); Mass spectrum (ESI⁻): m/z=282 [M−H]⁻.

EXAMPLE IX

Ethyl (2-Hydroxy-2-methyl-propylamino)-acetate 100.00 g of sodium carbonate are added with cooling to 50.00 g of glycine ethyl ester hydrochloride in 100 ml of saturated potassium carbonate solution. The mass formed is extracted several times with a total of about 600 ml of diethyl ether. The combined ether extracts are dried over sodium sulphate and evaporated to dryness. 28.60 g of glycine ethyl ester are left. This is mixed with 26.00 ml of isobutylene oxide and 40 ml of absolute ethanol and heated to 90° C. for six hours in a Roth bomb. After cooling to ambient temperature the reaction mixture is concentrated by evaporation, leaving a runny oil.

Yield: 45.80 g (73% of theory), Mass spectrum (ESI⁺): m/z=176 [M+H]⁺.

EXAMPLE X

4-Methylamino-dihydro-furan-2-one 2.00 g of 4-(N-benzyl-N-methyl-amino)-dihydro-furan-2-one in 25 ml methanol are hydrogenated in the presence of 250 mg of palladium (10% on activated charcoal) at a hydrogen pressure of 50 psi for about two hours at ambient temperature, until the calculated amount of hydrogen has been taken up. For working up the catalyst is filtered off and the filtrate is evaporated down in vacuo. A colourless oil remains, which is further reacted directly without any more purification.

Yield: 1.20 g; $R_f$ value: 0.13 (silica gel, ethyl acetate); Mass spectrum (ESI⁺): m/z=116 [M+H]⁺.

EXAMPLE XI 4-(N-benzyl-N-methyl-amino)-dihydro-furan-2-one 23.20 ml of N-methylbenzylamine are added to 15.00 g of 5H-furan-2-one in 150 ml methylene chloride. The reaction mixture is stirred for about 48 hours at ambient temperature. For working up the reaction mixture is concentrated by evaporation and chromatographed in batches over a silica gel column with ethyl acetate/petroleum ether (3:1) as eluant. The desired product is obtained as a yellowish oil.

Yield: 19.77g (54% of theory), $R_f$ value: 0.67 (silica gel, ethyl acetate); Mass spectrum (ESI$^+$): m/z=228 [M+Na]$^+$.

EXAMPLE XII

4-[(3-Chloro-4-fluorophenyl)amino]-7-cyclobutyloxy-6-hydroxy-quinazoline 10 ml of trifluoroacetic acid are added dropwise with stirring to 5.60 g of 6-benzyloxy4-[(3-chloro-4-fluorophenyl)amino]-7-cyclobutyloxy-quinazoline. The reaction mixture heats up to about 40° C. After 20 hours stirring at ambient temperature another 3 ml of trifluoroacetic acid are added. Since the reaction has scarcely progressed even after another three hours' stirring at ambient temperature, the reaction mixture is heated to 50° C. After four hours the reaction is complete and the excess trifluoroacetic acid is substantially distilled off using the rotary evaporator. The residue is mixed with water and made alkaline with concentrated aqueous ammonia solution. The light brown precipitate formed is suction filtered, washed with plenty of water and dried in the desiccator. The product obtained still contains trifluoroacetic acid.

Yield: 5.82 g; $R_f$ value: 0.61 (silica gel, methylene chloride/methanol=9:1); Mass spectrum (ESI$^+$): m/z=360, 362 [M+H]$^+$.

The following compounds are obtained analogously to Example XII:
(1) 4-[(3-Chloro-4-fluorophenyl)amino]-7-cyclopropylmethoxy-6-hydroxy-quinazoline $R_f$ value: 0.65 (silica gel, methylene chloride/methanol=9:1); Mass spectrum (ESI$^+$): m/z=360, 362 [M+H]$^+$.
(2) 4-[(3-Chloro-4-fluorophenyl)amino]-7-cyclopentyloxy-6-hydroxy-quinazoline $R_f$ value: 0.65 (silica gel, methylene chloride/methanol=9:1); Mass spectrum (ESI$^+$): m/z=374, 376 [M+H]$^+$.
(3) 4-[(3-Chloro-4-fluorophenyl)amino]-6-hydroxy-7-((R)-tetrahydrofuran-3-yloxy)-quinazoline $R_f$ value: 0.32 (silica gel, methylene chloride/methanol=9:1).
(4) 4-[(3-Chloro-4-fluorophenyl)amino]-6-hydroxy-7-[(R)-(tetrahydrofuran-2-yl)methoxy]-quinazoline Mass spectrum (ESI$^-$): m/z=388, 390 [M–H]$^-$.

EXAMPLE XIII

6-Benzyloxy4-[(3-chloro-4-fluorophenyl)amino]-7-cyclobutyloxy-quinazoline 7.50 g of potassium carbonate and 4.50 g of cyclobutyl methanesulphonate are added to 7.00 g of 6-benzyloxy4-[(3-chloro-4-fluorophenyl)amino]-7-hydroxy-quinazoline in 60 ml of N,N-dimethylformamide. The reaction mixture is stirred for two hours at 80° C. Then another 2.00 g of cyclobutyl methanesulphonate and 3.00 g of potassium carbonate are added and the mixture is stirred over the weekend at 60° C. As the reaction is still not complete, another 3.50 g of cyclobutyl methanesulphonate and 5.00 g of potassium carbonate are added. After a further 20 hours at 80° C. the reaction is almost finished. For working up the reaction mixture is combined with 300 ml of ethyl acetate and washed with water and saturated sodium chloride solution. The organic phase is dried over magnesium sulphate and concentrated by evaporation. The residue is stirred with methanol, producing a brownish precipitate. This is suction filtered, washed with methanol and dried in the desiccator.

Yield: 5.10 g of (64% of theory), $R_f$ value: 0.69 (silica gel, methylene chloride/methanol=9:1); Mass spectrum (ESI$^-$): m/z=448, 450 [M–H]$^-$.

The following compounds are obtained analogously to Example XIII:

(1) 6-Benzyloxy-4-[(3-chloro-4-fluorophenyl)amino]-7-cyclopropylmethoxy-quinazoline (Bromomethylcyclopropane is Used)

$R_f$ value: 0.72 (silica gel, methylene chloride/methanol=9:1); Mass spectrum (ESI$^-$): m/z=448, 450 [M–H]$^-$.
(2) 6-Benzyloxy-4-[(3-chloro-4-fluorophenyl)amino]-7-cyclopentyloxy-quinazoline (Bromocyclopentane is Used)

$R_f$ value: 0.78 (silica gel, methylene chloride/methanol=9:1); Mass spectrum (ESI$^+$): m/z=464, 466 [M+H]$^+$.

EXAMPLE XIV tert.Butyl (S)-(2-Hydroxy-propylamino)-acetate 15.00 g of (S)-(+)-1-amino-2-propanol are dissolved in 100 ml of N,N-dimethylformamide and 6.97 ml of diisopropylethylamine are added. Then 5.91 ml of tert.butyl bromoacetate are added dropwise thereto within 30 minutes while cooling with an ice bath. The cooling bath is removed and the reaction mixture is stirred overnight at ambient temperature. For working up the reaction mixture is evaporated down in vacuo. The flask residue is dissolved in 50 ml water and saturated with 15 g of sodium chloride. The aqueous solution is extracted several times with ethyl acetate. The combined extracts are washed with saturated sodium chloride solution, dried over magnesium sulphate and evaporated down in vacuo, leaving a yellowish oil.

Yield: 7.36 g of (97% of theory), $R_f$ value: 0.46 (silica gel, ethyl acetate/methanol=9:1); Mass spectrum (ESI$^+$): m/z=190 [M+H]$^+$.

The following compounds are obtained analogously to Example XIV:
(1) tert. Butyl (R)-(2-Hydroxy-propylamino)-acetate $R_f$ value: 0.46 (silica gel, ethyl acetate/methanol=9:1); Mass spectrum (ESI$^+$): m/z=190 [M+H]$^+$.
(2) tert.Butyl (1,1-Dimethyl-2-hydroxy-ethylamino)-acetate Mass spectrum (ESI$^+$): m/z=204 [M+H]$^+$; $R_f$ value: 0.47 (silica gel, methylene chloride/methanol/conc. aqueous ammonia solution=90:10:0.1).

EXAMPLE XV

4-[(3-Chloro-4-fluorophenyl)amino]-6-(3-methanesulphonyloxy-propyloxy)-7-cyclobutyloxy-quinazoline The compound is obtained by reacting 4-[(3-chloro-4-fluorophenyl)amino]-6-(3-hydroxy-propyloxy)-7-cyclobutyloxy-quinazoline with methanesulphonic acid chloride in methylene chloride in the presence of diisopropylethylamine at ambient temperature.

$R_f$ value: 0.37 (silica gel, methylene chloride/methanol=95:5); Mass spectrum (ESI$^-$): m/z=494, 496 [M–H]$^-$.

The following compounds are obtained analogously to Example XV:
(1) 4-[(3-Chloro-4-fluorophenyl)amino]-6-(3-methanesulphonyloxy-propyloxy)-7-cyclopropylmethoxy-quinazoline $R_f$ value: 0.65 (silica gel, methylene chloride/methanol=90:10); Mass spectrum (ESI$^-$): m/z=494, 496 [M–H]$^-$.
(2) 4-[(3-Chloro-4-fluorophenyl)amino]-6-cyclopropylmethoxy-7-(3-methanesulphonyloxy-propyloxy)-quinazoline $R_f$ value: 0.73 (silica gel, methylene chloride/methanol=90:10); Mass spectrum (ESI$^+$): m/z=496, 498 [M+H]$^+$.
(3) 4-[(3-Chloro-4-fluorophenyl)amino]-6-(4-methanesulphonyloxy-butyloxy)-7-cyclopentyloxy-quinazoline $R_f$ value: 0.76 (silica gel, methylene chloride/methanol=90:10); Mass spectrum (ESI$^+$): m/z=524, 526 [M+H]$^+$.

EXAMPLE XVI

4-[(3-Chloro-4-fluorophenyl)amino]-6-hydroxy-7-cyclopropylmethoxy-quinazoline

The compound is obtained by hydrogenation of 6-benzyloxy-4-[(3-chloro-4-fluorophenyl)amino]-7-cyclopropylmethoxy-quinazoline in the presence of 10% Pd/C in a mixture of methylene chloride, ethanol and conc. hydrochloric acid (500:210:3.5) in a Parr apparatus.

Yield: 73% of theoretical; Mass spectrum (ESI$^+$): m/z=360, 362 [M+H]$^+$.

EXAMPLE XVII

Cyclopentyl 5-Benzyloxy4-cyclopentyloxy-2-nitro-benzoate

The compound is obtained by reacting 5-benzyloxy4-hydroxy-2-nitro-benzoic acid with 2.2 equivalents of bromocyclopentane in the presence of potassium carbonate as auxiliary base in dimethyl sulphoxide at ambient temperature.

Yield: 87% of theoretical; R$_f$ value: 0.92 (silica gel, ethyl acetate/cyclohexane=1:1); Mass spectrum (ESI$^+$): m/z=426 [M+H]$^+$.

EXAMPLE XVIII

4-[(3-Chloro-4-fluorophenyl)amino]-6-benzyloxy-7-((R)-tetrahydrofuran-3-yloxy)quinazoline 5.03 ml of diethyl azodicarboxylate are added dropwise to a solution of 8.00 g of 4-[(3-chloro-4-fluorophenyl)amino]-6-benzyloxy-7-hydroxy-quinazoline (see WO0055141 A1) and 2.42 ml of (S)-(+)-3-hydroxy-tetrahydrofuran and 7.95 g of triphenylphosphine in 160 ml of tetrahydrofuran. The reaction mixture is stirred overnight at ambient temperature and then evaporated down using the rotary evaporator. The flask residue is purified by chromatography over a silica gel column with methylene chloride/ethyl acetate (gradient from 2:1 to 1:2) as eluant.

Yield: 7.34 g (78% of theoretical); Melting point: 165–168° C.; Mass spectrum (ESI$^+$): m/z=466, 468 [M+H]$^+$.

The following compounds are obtained analogously to Example XVIII:
(1) 4-[(3-Chloro-4-fluorophenyl)amino]-6-benzyloxy-7-[(R)-(tetrahydrofuran-2-yl)methoxy]-quinazoline Mass spectrum (ESI$^+$): m/z=480, 482 [M+H]$^+$; R$_f$ value: 0.38 (silica gel, methylene chloride/methanol=15:1).

(2) 4-[(3-Chloro-4-fluorophenyl)amino]-7-(2-bromo-ethoxy)-6-((S)-tetrahydrofuran-3-yloxy)-quinazoline R$_f$ value: 0.35 (silica gel, methylene chloride/methanol=20:1).

Preparation of the Final Compounds:

EXAMPLE 1

4-[(3-Chloro-4-fluorophenyl)amino]-6-cyclopentylmethoxy-7-[2-(6,6-dimethyl-2-oxo-morpholin-4-yl)-ethoxy]-quinazoline 250 mg of 4-[(3-chloro-4-fluorophenyl)amino]-6-cyclopentylmethoxy-7-(2-bromoethoxy)-quinazoline and 341 mg of ethyl (2-hydroxy-2-methyl-propylamino)-acetate are dissolved in 20 ml acetonitrile and combined with 50 mg of sodium iodide, 275 mg of potassium carbonate and 0.70 ml of diisopropylethylamine. The reaction mixture is refluxed for about 90 hours. After cooling to ambient temperature the reaction mixture is filtered and the filtrate is evaporated down in vacuo. The flask residue is chromatographed over a silica gel column with petroleum ether/ethyl acetate (50:50, later 0:100) as eluant. The cyclised product is obtained as a beige solid.

Yield: 62 mg (23% of theory), R$_f$ value: 0.29 (silica gel, ethyl acetate); Mass spectrum (ESI$^-$): m/z=541, 543 [M–H]$^-$.

The following compounds are obtained analogously to Example 1:
(1) 4-[(3-Chloro-4-fluorophenyl)amino]-6-cyclopropylmethoxy-7-[2-(6,6-dimethyl-2-oxo-morpholin-4-yl)-ethoxy]-quinazoline R$_f$ value: 0.58 (silica gel, methylene chloride/methanol=9:1); Mass spectrum (ESI$^-$): m/z=513, 515 [M–H]$^-$.

(2) 4-[(3-Chloro-4-fluorophenyl)amino]-7-cyclobutyloxy-6-[3-(6,6-dimethyl-2-oxo-morpholin-4-yl)-propyloxy]-quinazoline Melting point: 212–214° C.; Mass spectrum (ESI$^-$): m/z=527, 529 [M–H]$^-$.

(3) 4-[(3-Chloro-4-fluorophenyl)amino]-7-cyclopropylmethoxy-6-[3-(6,6-dimethyl-2-oxo-morpholin-4-yl)-propyloxyl-quinazoline Melting point: 200–202° C.; Mass spectrum (ESI$^-$): m/z=527, 529 [M–H]$^-$.

(4) 4-[(3-Chloro-4-fluorophenyl)amino]-6-[3-(6,6-dimethyl-2-oxo-morpholin-4-yl)-propyloxy]-7-methoxy-guinazoline Melting point: 222–224° C.; Mass spectrum (ESI$^-$): m/z=487, 489 [M–H]$^-$.

EXAMPLE 2

4-[(3-Chloro-4-fluorophenyl)amino]-6-cyclopropylmethoxy-7-{2-[N-(2-oxo-tetrahydrofuran-4-yl)-N-methyl-amino]-ethoxy}-quinazoline 300 mg of 4-[(3-chloro-4-fluorophenyl)amino]-6-cyclopropylmethoxy-7-(2-bromoethoxy)-quinazoline and 400 mg of 4-methylamino-dihydro-furan-2-one in 20 ml acetonitrile are combined with 240 mg of potassium carbonate and 70 mg of sodium iodide and refluxed for 24 hours. After cooling to ambient temperature the reaction mixture is filtered and the filtrate is evaporated down in vacuo. The flask residue is chromatographed over a silica gel column with methylene chloride/methanol/concentrated aqueous ammonia solution (97:3:0.05) as eluant. The title compound is obtained as a light beige solid.

Yield: 70 mg (22% of theory), R$_f$ value: 0.47 (silica gel, methylene chloride/methanol/concentrated aqueous ammonia solution=90:10:0.1); Mass spectrum (ESI$^+$): m/z=501, 503 [M+H]$^+$.

The following compounds are obtained analogously to Example 2:
(1) 4-[(3-Chloro-4-fluorophenyl)amino]-6-cyclopentyloxy-7-{2-[N-(2-oxo-tetrahydrofuran-4-yl)-N-methyl-amino]-ethoxy}-quinazoline R$_f$ value: 0.42 (silica gel, methylene chloride/methanol/concentrated aqueous ammonia solution=90:10:0.1); Mass spectrum (ESI$^+$): m/z=515, 517 [M+H]$^+$.

(2) 4-[(3-Chloro-4-fluorophenyl)amino]-6-{ 3-[N-(2-oxo-tetrahydrofuran-4-yl)-N-methyl-amino]-propyloxy}-7-cyclobutyloxy-quinazoline Melting point: 147.5–151° C.; Mass spectrum (ESI$^+$): m/z=515, 517 [M+H]$^+$.

EXAMPLE 3

4-[(3-Bromo-phenyl)amino]-6-[2-((S)-6-methyl-2-oxo-morpholin-4-yl)-ethoxy]-7-methoxy-quinazoline 90 μl of methanesulphonic acid are added to 380 mg of 4-[(3-bromo-phenyl)amino]-6-(2-{N-

[(tert.butyloxycarbonyl)methyl]-N-((S)-2-hydroxy-propyl)-amino}-ethoxy)-7-methoxy-quinazoline in 8 ml of acetonitrile. The reaction mixture is refluxed for about three hours, then another equivalent of methanesulphonic acid is added and refluxing is continued until the reaction is complete. For working up the reaction mixture is diluted with ethyl acetate and washed with saturated sodium hydrogen carbonate solution and saturated sodium chloride solution. The organic phase is dried over magnesium sulphate and evaporated down in vacuo. The flask residue is stirred with diethylether and suction filtered. The title compound is obtained as a white solid.

Yield: 280 mg (85% of theory), Melting point: 190° C.; Mass spectrum (ESI$^-$): m/z=485, 487 [M–H]$^-$.

The following compounds are obtained analogously to Example 3:

(1) 4-[(3-Bromo-phenyl)amino]-6-[2-((R)-6-methyl-2-oxo-morpholin-4-yl)-ethoxy]-7-methoxy-quinazoline Melting point: 193° C.; Mass spectrum (ESI$^+$): m/z=487, 489 [M+H]$^+$.

(2) 4-[(3-Chloro-4-fluorophenyl)amino]-6-[2-((R)-6-methyl-2-oxo-morpholin-4-yl)-ethoxy]-7-methoxy-quinazoline (The Reaction is Carried out with Trifluoroacetic Acid in Acetonitrile)

Melting point: 208° C.; Mass spectrum (ESI$^-$): m/z=459, 461 [M–H]$^-$.

(3) 4-[(3-Chloro-4-fluorophenyl)amino]-6-[3-((R)-6-methyl-2-oxo-morpholin-4-yl)-propyloxy]-7-methoxy-quinazoline (The Reaction is Carried out with Trifluoroacetic Acid in Acetonitrile)

R$_f$ value: 0.33 (silica gel, ethyl acetate); Mass spectrum (ESI$^-$): m/z=473, 475 [M–H]$^-$.

(4) 4-[(R)-(1-Phenyl-ethyl)amino]-6-[3-((S)-6-methyl-2-oxo-morpholin-4-yl)-propyloxy]-7-methoxy-quinazoline (The Reaction is Carried out with Trifluoroacetic Acid in Acetonitrile)

R$_f$ value: 0.41 (silica gel, ethyl acetate/methanol=9:1); Mass spectrum (ESI$^-$): m/z=449 [M–H]$^-$.

(5) 4-[(R)-(1-phenyl-ethyl)amino]-6-[2-((S)-6-methyl-2-oxo-morpholin-4-yl)-ethoxy]-7-methoxy-quinazoline (The Reaction is Carried out with Trifluoroacetic Acid in Acetonitrile)

R$_f$ value: 0.49 (silica gel, ethyl acetate/methanol/concentrated aqueous ammonia solution=9:1:0.1); Mass spectrum (ESI$^-$): m/z=435 [M–H]$^-$.

(6) 4-[(3-Chloro-4-fluorophenyl)amino]-6-[3-((R)-6-methyl-2-oxo-morpholin-4-yl)-propyloxy]-7-cyclobutyloxy-quinazoline (The Reaction is Carried out with Trifluoroacetic Acid in Acetonitrile)

Melting point: 185.5–189.5° C.; Mass spectrum (ESI$^+$): m/z=515, 517 [M+H]$^+$.

(7) 4-[(3-Chloro-4-fluorophenyl)amino]-6-[3-(5,5-dimethyl-2-oxo-morpholin-4-yl)-propyloxy]-7-cyclobutyloxy-quinazoline (The Reaction is Carried out with Trifluoroacetic Acid in Acetonitrile)

Melting point: 214–216° C.; Mass spectrum (ESI$^-$): m/z=527, 529 [M–H]$^-$.

(8) 4-[(3-Chloro-4-fluorophenyl)amino]-6-[3-((R)-6-methyl-2-oxo-morpholin-4-yl)-propyloxy]-7-cyclopropylmethoxy-quinazoline (The Reaction is Carried out with Trifluoroacetic Acid in Acetonitrile)

Melting point: 160.5–163° C.; Mass spectrum (ESI$^+$): m/z=515, 517 [M+H]$^+$.

(9) 4-[(3-Chloro-4-fluorophenyl)amino]-6-[3-((S)-6-methyl-2-oxo-morpholin-4-yl)-propyloxy]-7-cyclopropylmethoxy-quinazoline (The Reaction is Carried out with Trifluoroacetic Acid in Acetonitrile)

Melting point: 160–162° C.; Mass spectrum (ESI$^+$): m/z=515, 517 [M+H]$^+$.

(10) 4-[(3-Chloro-4-fluorophenyl)amino]-6-[2-((S)-6-methyl-2-oxo-morpholin-4-yl)-ethoxy]-7-cyclopentyloxy-quinazoline (The Reaction is Carried out with Trifluoroacetic Acid in Acetonitrile)

R$_f$ value: 0.31 (silica gel, ethyl acetate); Mass spectrum (ESI$^+$): m/z=515, 517 [M+H]$^+$.

(11) 4-[(3-Chloro-4-fluorophenyl)amino]-6-[2-((R)-6-methyl-2-oxo-morpholin-4-yl)-ethoxy]-7-cyclopentyloxy-quinazoline (The Reaction is Carried out with Trifluoroacetic Acid in Acetonitrile)

Melting point: 176–178° C.; Mass spectrum (ESI$^+$): m/z=515, 517 [M+H]$^+$.

(12) 4-[(3-Chloro-4-fluorophenyl)amino]-6-[2-((S)-6-methyl-2-oxo-morpholin-4-yl)-ethoxy]-7-cyclopropylmethoxy-quinazoline (The Reaction is Carried out with Trifluoroacetic Acid in Acetonitrile)

R$_f$ value: 0.37 (silica gel, ethyl acetate); Mass spectrum (ESI$^+$): m/z=501, 503 [M+H]$^+$.

(13) 4-[(3-Chloro-4-fluorophenyl)amino]-6-[2-((R)-6-methyl-2-oxo-morpholin-4-yl)-ethoxy]-7-cyclopropylmethoxy-quinazoline (The Reaction is Carried out with Trifluoroacetic Acid in Acetonitrile)

R$_f$ value: 0.37 (silica gel, ethyl acetate); Mass spectrum (ESI$^+$): m/z=501, 503 [M+H]$^+$.

(14) 4-[(3-Chloro-4-fluorophenyl)amino]-6-cyclopropylmethoxy-7-[2-((S)-6-methyl-2-oxo-morpholin-4-yl)-ethoxy]-quinazoline (The Reaction is Carried out with Trifluoroacetic Acid in Acetonitrile)

R$_f$ value: 0.48 (silica gel, ethyl acetate/methanol=9:1); Mass spectrum (ESI$^+$): m/z=501, 503 [M+H]$^+$.

(15) 4-[(3-Chloro-4-fluorophenyl)amino]-6-cyclopropylmethoxy-7-[2-((R)-6-methyl-2-oxo-morpholin-4-yl)-ethoxy]-quinazoline (The Reaction is Carried out with Trifluoroacetic Acid in Acetonitrile)

Mass spectrum (ESI$^+$): m/z=501, 503 [M+H]$^+$.

(16) 4-[(3-Chloro-4-fluorophenyl)amino]-6-cyclopropylmethoxy-7-[3-((R)-6-methyl-2-oxo-morpholin-4-yl)-propyloxy]-quinazoline (The Reaction is Carried out with Trifluoroacetic Acid in Acetonitrile)

R$_f$ value: 0.67 (silica gel, ethyl acetate/methanol=9:1); Mass spectrum (ESI$^-$): m/z=513, 515 [M–H]$^-$.

(17) 4-[(3-Chloro-4-fluorophenyl)amino]-6-cyclopropylmethoxy-7-[3-((S)-6-methyl-2-oxo-morpholin-4-yl)-propyloxy]-quinazoline (The Reaction is Carried out with Trifluoroacetic Acid in Acetonitrile)

R$_f$ value: 0.67 (silica gel, ethyl acetate/methanol=9:1); Mass spectrum (ESI$^-$): m/z=513, 515 [M–H]$^-$.

(18) 4-[(3-chloro-4-fluorophenyl)amino]-6-[2-(6,6-dimethyl-2-oxo-morpholin-4-yl)-ethoxy]-7-cyclopentyloxy-quinazoline (The Reaction is Carried out with Trifluoroacetic Acid in Acetonitrile)

R$_f$ value: 0.56 (silica gel, ethyl acetate); Mass spectrum (ESI$^+$): m/z=529, 531 [M+H]$^+$.

(19) 4-[(3-Chloro-4-fluorophenyl)amino]-6-cyclopentyloxy-7-[2-((S)-6-methyl-2-oxo-morpholin-4-yl)-ethoxy]-quinazoline (The Reaction is Carried out with Trifluoroacetic Acid in Acetonitrile)

R$_f$ value: 0.60 (silica gel, ethyl acetate/methanol=9:1); Mass spectrum (ESI$^+$): m/z=515, 517 [M+H]$^+$.

(20) 4-[(3-Chloro-4-fluorophenyl)amino]-6-cyclopentyloxy-7-[2-((R)-6-methyl-2-oxo-morpholin-4-yl)-ethoxy]-quinazoline (The Reaction is Carried out with Trifluoroacetic Acid in Acetonitrile)

Mass spectrum (ESI$^+$): m/z=515, 517 [M+H]$^+$.

(21) 4-[(3-Chloro-4-fluorophenyl)amino]-6-[4-((S)-6-methyl-2-oxo-morpholin-4-yl)-butyloxy]-7-cyclopentyloxy-quinazoline (The Reaction is Carried out with Trifluoroacetic Acid in Acetonitrile)

R$_f$ value: 0.51 (silica gel, ethyl acetate); Mass spectrum (ESI$^+$): m/z=543, 545 [M+H]$^+$.

(22) 4-[(3-Chloro-4-fluorophenyl)amino]-6-[4-((R)-6-methyl-2-oxo-morpholin-4-yl)-butyloxy]-7-cyclopentyloxy-quinazoline (The Reaction is Carried out with Trifluoroacetic Acid in Acetonitrile)

Mass spectrum (ESI+): m/z=543, 545 [M+H]+.

(23) 4-[(3-Chloro-4-fluorophenyl)amino]-6-[3-((S)-6-methyl-2-oxo-morpholin-4-yl)-propyloxy]-7-methoxy-quinazoline (The Reaction is Carried out with Trifluoroacetic Acid in Acetonitrile)

Melting point: 183–186° C.; Mass spectrum (ESI+): m/z= 475, 477 [M+H]+.

(24) 4-[(3-Chloro-4-fluorophenyl)amino]-6-[3-(5,5-dimethyl-2-oxo-morpholin-4-yl)-propyloxy]-7-methoxy-quinazoline (The Reaction is Carried out with Trifluoroacetic Acid in Acetonitrile)

$R_f$ value: 0.43 (silica gel, ethyl acetate); Mass spectrum (ESI−): m/z=487, 489 [M−H]−.

(25) 4-[(3-Chloro-4-fluorophenyl)amino]-6-[2-((S)-6-methyl-2-oxo-morpholin-4-yl)-ethoxy]-7-methoxy-quinazoline (The Reaction is Carried out with Trifluoroacetic Acid in Acetonitrile)

Melting point: 212–213° C.; Mass spectrum (ESI+): m/z= 461, 463 [M+H]+.

(26) 4-[(3-Chloro-4-fluorophenyl)amino]-6-{2-[N-(carboxymethyl)-N-((S)-2-hydroxy-propyl)-amino]-ethoxy}-7-methoxy-quinazoline (By-product of the Production of 3(25))

Melting point: 187–190° C.; Mass spectrum (ESI+): m/z= 479, 481 [M+H]+.

(27) 4-[(3-Chloro-4-fluorophenyl)amino]-6-[2-(6,6-dimethyl-2-oxo-morpholin-4-yl)-ethoxy]-7-methoxy-quinazoline (The Reaction is Carried out with Trifluoroacetic Acid in Acetonitrile)

Melting point: 229–232° C.; Mass spectrum (ESI−): m/z= 473, 475 [M−H]−.

(28) 4-[(3-chloro-4-fluorophenyl)amino]-6-[2-(6,6-dimethyl-2-oxo-morpholin-4-yl)-ethoxy]-7-((R)-tetrahydrofuran-3-yloxy)-quinazoline (The Reaction is Carried out with Trifluoroacetic Acid in Acetonitrile)

Melting point: 195–196° C.; Mass spectrum (ESI+): m/z= 531, 533 [M+H]+.

(29) 4-[(3-chloro-4-fluorophenyl)amino]-6-[2-(6,6-dimethyl-2-oxo-morpholin-4-yl)-ethoxy]-7-[(R)-(tetrahydrofuran-2-yl)methoxy]-quinazoline (The Reaction is Carried out with Trifluoroacetic Acid in Acetonitrile)

Melting point: 184° C.; Mass spectrum (ESI+): m/z=545, 547 [M+H]+.

(30) 4-[(3-chloro-4-fluorophenyl)amino]-7-[2-(6,6-dimethyl-2-oxo-morpholin-4-yl)-ethoxy]-6-((S)-tetrahydrofuran-3-yloxy)-quinazoline Melting point: 202–205° C.; Mass spectrum (ESI+): m/z= 531, 533 [M+H]+.

(31) 4-[(3-chloro-4-fluorophenyl)amino]-7-[2-(6,6-dimethyl-2-oxo-morpholin-4-yl)-ethoxy]-6-[(S)-(tetrahydrofuran-2-yl)methoxy]-quinazoline Melting point: 182° C.; Mass spectrum (ESI+): m/z=545, 547 [M+H]+.

EXAMPLE 4

4-[(3-Bromo-phenyl)amino]-6-(2-{N-[(tert.butyloxycarbonyl)methyl]-N-((S)-2-hydroxy-propyl)-amino}-ethoxy)-7-methoxy-quinazoline 0.25 ml of diisopropylethylamine are added to 650 mg of 4-[(3-bromo-phenyl)amino]-6-(2-bromoethoxy)-7-methoxy-quinazoline and 1.10 g of tert.butyl (S)-(2-hydroxy-propylamino)-acetate in 15 ml of acetonitrile. The reaction mixture is stirred overnight at 50° C. Since no reaction can be detected, the reaction mixture is concentrated by evaporation, combined with 20 ml of N,N-dimethylformamide and stirred for eight hours at 60° C. Then the temperature is increased to 80° C. After another eight hours the reaction is complete. The reaction mixture is concentrated by evaporation and chromatographed over a silica gel column with ethyl acetate as eluant. The desired product is obtained as a white solid.

Yield: 410 mg (51% of theory), $R_f$ value: 0.27 (silica gel, ethyl acetate); Mass spectrum (ESI−): m/z=559, 561 [M−H]−.

The following compounds are obtained analogously to Example 4:

(1) 4-[(3-Bromo-phenyl)amino]-6-(2-{N-[(tert.butyloxycarbonyl)methyl]-N-((R)-2-hydroxy-propyl)-amino}-ethoxy)-7-methoxy-quinazoline Melting point: 130° C.; Mass spectrum (ESI−): m/z=559, 561 [M−H]−.

(2) 4-[(3-Chloro-4-fluorophenyl)amino]-6-(2-{N-[(tert.butyloxycarbonyl)methyl]-N-((R)-2-hydroxy-propyl)-amino}-ethoxy)-7-methoxy-quinazoline (The Reaction is Carried out in N,N-dimethylformamide)

$R_f$ value: 0.40 (silica gel, ethyl acetate/petroleum ether= 4:1);

(3) 4-[(3-Chloro-4-fluorophenyl)amino]-6-(3-{N-[(tert.butyloxycarbonyl)methyl]-N-((R)-2-hydroxy-propyl)-amino}-propyloxy)-7-methoxy-quinazoline (The Reaction is Carried out in N,N-dimethylformamide)

$R_f$ value: 0.37 (silica gel, ethyl acetate/petroleum ether= 4:1); Mass spectrum (ESI−): m/z=547, 549 [M−H]−.

(4) 4-[(R)-(1-Phenyl-ethyl)amino]-6-(3-{N-[(tert.butyloxycarbonyl)methyl]-N-((S)-2-hydroxy-propyl)-amino}-propyloxy)-7-methoxy-quinazoline (The Reaction is Carried out in N,N-dimethylformamide)

$R_f$ value: 0.65 (silica gel, ethyl acetate/methanol=9:1); Mass spectrum (EI): m/z=524 [M]+.

(5) 4-[(R)-(1-Phenyl-ethyl)amino]-6-(2-{N-[(tert.butyloxycarbonyl)methyl]-N-((S)-2-hydroxy-propyl)-amino}-ethoxy)-7-methoxy-quinazoline (The Reaction is Carried out in N,N-dimethylformamide)

$R_f$ value: 0.57 (silica gel, ethyl acetate/methanol/ concentrated aqueous ammonia solution=9:1:0.1).

(6) 4-[(3-Chloro-4-fluorophenyl)amino]-6-(3-{N-[(tert.-butyloxycarbonyl)methyl]-N-((R)-2-hydroxy-propyl)-amino}-propyloxy)-7-cyclobutyloxy-quinazoline $R_f$ value: 0.31 (silica gel, methylene chloride/methanol= 95:5).

(7) 4-[(3-Chloro-4-fluorophenyl)amino]-6-(3-{N-[(tert.-butyloxycarbonyl)methyl]-N-(1,1-dimethyl-2-hydroxy-ethyl)-amino}-propyloxy)-7-cyclobutyloxy-quinazoline $R_f$ value: 0.29 (silica gel, methylene chloride/methanol= 95:5); Mass spectrum (ESI+): m/z=603, 605 [M+H]+.

(8) 4-[(3-Chloro-4-fluorophenyl)amino]-6-(3-{N-[(tert.-butyloxycarbonyl)methyl]-N-((R)-2-hydroxy-propyl)-amino}-propyloxy)-7-cyclopropylmethoxy-quinazoline $R_f$ value: 0.37 (silica gel, methylene chloride/methanol= 95:5).

(9) 4-[(3-Chloro-4-fluorophenyl)amino]-6-(3-{N-[(tert.-butyloxycarbonyl)methyl]-N-((S)-2-hydroxy-propyl)-amino}-propyloxy)-7-cyclopropylmethoxy-quinazoline $R_f$ value: 0.50 (silica gel, ethyl acetate).

(10) 4-[(3-Chloro-4-fluorophenyl)amino]-6-(2-{N-[(tert.-butyloxycarbonyl)methyl]-N-((S)-2-hydroxy-propyl)-amino}-ethoxy)-7-cyclopentyloxy-quinazoline $R_f$ value: 0.54 (silica gel, ethyl acetate/cyclohexane=9:1).

(11) 4-[(3-Chloro-4-fluorophenyl)amino]-6-(2-{N-[(tert.-butyloxycarbonyl)methyl]-N-((R)-2-hydroxy-propyl)-amino}-ethoxy)-7-cyclopentyloxy-quinazoline $R_f$ value: 0.66 (silica gel, ethyl acetate).

(12) 4-[(3-Chloro-4-fluorophenyl)amino]-6-(2-{N-[(tert.-butyloxycarbonyl)methyl]-N-((S)-2-hydroxy-propyl)-amino}-ethoxy)-7-cyclopropylmethoxy-quinazoline $R_f$ value: 0.60 (silica gel, ethyl acetate).

(13) 4-[(3-Chloro-4-fluorophenyl)amino]-6-(2-{N-[(tert.-butyloxycarbonyl)methyl]-N-((R)-2-hydroxy-propyl)-amino}-ethoxy)-7-cyclopropylmethoxy-quinazoline $R_f$ value: 0.60 (silica gel, ethyl acetate).

(14) 4-[(3-Chloro-4-fluorophenyl)amino]-6-cyclopropylmethoxy-7-(2-{N-[(tert.-butyloxycarbonyl)methyl]-N-((S)-2-hydroxy-propyl)-amino}-ethoxy)-quinazoline $R_f$ value: 0.30 (silica gel, ethyl acetate).

(15) 4-[(3-Chloro-4-fluorophenyl)amino]-6-cyclopropylmethoxy-7-(2-{N-[(tert.-butyloxycarbonyl)methyl]-N-((R)-2-hydroxy-propyl)-amino}-ethoxy)-quinazoline $R_f$ value: 0.30 (silica gel, ethyl acetate).

(16) 4-[(3-Chloro-4-fluorophenyl)amino]-6-cyclopropylmethoxy-7-(3-{N-[(tert.-butyloxycarbonyl)methyl]-N-((R)-2-hydroxy-propyl)-amino}-propyloxy)-quinazoline $R_f$ value: 0.35 (silica gel, ethyl acetate).

(17) 4-[(3-Chloro-4-fluorophenyl)amino]-6-cyclopropylmethoxy-7-(3-{N-[(tert.-butyloxycarbonyl)methyl]-N-((S)-2-hydroxy-propyl)-amino}-propyloxy])-quinazoline $R_f$ value: 0.35 (silica gel, ethyl acetate).

(18) 4-[(3-Chloro-4-fluorophenyl)amino]-6-(2-{N-[(ethoxycarbonyl)methyl]-N-(2-hydroxy-2-methyl-propyl)-amino}-ethoxy)-7-cyclopentyloxy-quinazoline $R_f$ value: 0.64 (silica gel, methylene chloride/methanol=9:1); Mass spectrum (ESI$^+$): m/z=575, 577 [M+H]$^+$.

(19) 4-[(3-Chloro-4-fluorophenyl)amino]-6-cyclopentyloxy-7-(2-{N-[(tert.-butyloxycarbonyl)methyl]-N-((S)-2-hydroxy-propyl)-amino}-ethoxy)-quinazoline $R_f$ value: 0.51 (silica gel, ethyl acetate).

(20) 4-[(3-Chloro-4-fluorophenyl)amino]-6-cyclopentyloxy-7-(2-{N-[(tert.-butyloxycarbonyl)methyl]-N-((R)-2-hydroxy-propyl)-amino}-ethoxy)-quinazoline $R_f$ value: 0.51 (silica gel, ethyl acetate).

(21) 4-[(3-Chloro-4-fluorophenyl)amino]-6-(4-{N-[(tert.-butyloxycarbonyl)methyl]-N-((S)-2-hydroxy-propyl)-amino}-butyloxy)-7-cyclopentyloxy-quinazoline $R_f$ value: 0.61 (silica gel, ethyl acetate).

(22) 4-[(3-Chloro-4-fluorophenyl)amino]-6-(4-{N-[(tert.-butyloxycarbonyl)methyl]-N-((R)-2-hydroxy-propyl)-amino}-butyloxy)-7-cyclopentyloxy-quinazoline $R_f$ value: 0.61 (silica gel, ethyl acetate).

(23) 4-[(3-Chloro-4-fluorophenyl)amino]-6-(3-{N-[(tert.-butyloxycarbonyl)methyl]-N-((S)-2-hydroxy-propyl)-amino}-propyloxy)-7-methoxy-quinazoline $R_f$ value: 0.46 (silica gel, ethyl acetate); Mass spectrum (ESI$^-$): m/z=547, 549 [M−H]$^-$.

(24) 4-[(3-Chloro-4-fluorophenyl)amino]-6-(3-{N-[(tert.-butyloxycarbonyl)methyl]-N-(1,1-dimethyl-2-hydroxy-ethyl)-amino}-propyloxy)-7-methoxy-quinazoline Mass spectrum (ESI$^+$): m/z=563, 565 [M+H]$^+$.

(25) 4-[(3-Chloro-4-fluorophenyl)amino]-6-(2-{N-[(tert.-butyloxycarbonyl)methyl]-N-((S)-2-hydroxy-propyl)-amino}-ethoxy)-7-methoxy-quinazoline $R_f$ value: 0.66 (silica gel, ethyl acetate/methanol=9:1); Mass spectrum (ESI$^+$): m/z=535, 537 [M+H]$^+$.

(26) 4-[(3-Chloro-4-fluorophenyl)amino]-6-(2-{N-[(ethoxycarbonyl)methyl]-N-(2-hydroxy-2-methyl-propyl)-amino}-ethoxy)-7-methoxy-quinazoline (Occurs as a Mixture with Substance Already Cyclised)

$R_f$ value: 0.44 (silica gel, ethyl acetate); Mass spectrum (ESI$^+$): m/z=521, 523 [M+H]$^+$.

(27) 4-[(3-Chloro-4-fluorophenyl)amino]-6-(2-{N-[(ethoxycarbonyl)methyl]-N-(2-hydroxy-2-methyl-propyl)-amino}-ethoxy)-7-((R)-tetrahydrofuran-3-yloxy)-quinazoline (Occurs as a Mixture with Substance Already Cyclised)

$R_f$ value: 0.30 (silica gel, methylene chloride/methanol=9:1).

(28) 4-[(3-Chloro-4-fluorophenyl)amino]-6-(2-{N-[(ethoxycarbonyl)methyl]-N-(2-hydroxy-2-methyl-propyl)-amino}-ethoxy)-7-[(R)-(tetrahydrofuran-2-yl)methoxy]-quinazoline Mass spectrum (ESI$^-$): m/z=589, 591 [M−H]$^-$.

(29) 4-[(3-Chloro-4-fluorophenyl)amino]-7-(2-{N-[(ethoxycarbonyl)methyl]-N-(2-hydroxy-2-methyl-propyl)-amino}-ethoxy)-6-((S)-tetrahydrofuran-3-yloxy)-quinazoline $R_f$ value: 0.16 (silica gel, methylene chloride/methanol=20:1).

(30) 4-[(3-Chloro-4-fluorophenyl)amino]-7-(2-{N-[(ethoxycarbonyl)methyl]-N-(2-hydroxy-2-methyl-propyl)-amino}-ethoxy)-6-[(S)-(tetrahydrofuran-2-yl)methoxy]-quinazoline $R_f$ value: 0.68 (silica gel, ethyl acetate/methanol=15:1).

The following compounds may be prepared analogously to the preceding Examples and other methods known from the literature:

(1) 4-[(3-Chloro-4-fluorophenyl)amino]-7-[2-(6-methyl-2-oxo-morpholin-4-yl)-ethoxy]-6-methoxy-quinazoline (2) 4-[(3-Chloro-4-fluorophenyl)amino]-7-[3-(6-methyl-2-oxo-morpholin-4-yl)-propyloxy]-6-methoxy-quinazoline (3) 4-[(3-Chloro-4-fluorophenyl)amino]-6-[2-((S)-6-methyl-2-oxo-morpholin-4-yl)-ethoxy]-7-methoxy-quinazoline (4) 4-[(3-Chloro-4-fluorophenyl)amino]-6-[3-((S)-6-methyl-2-oxo-morpholin-4-yl)-propyloxy]-7-methoxy-quinazoline (5) 4-[(3-Chloro-4-fluorophenyl)amino]-6-[3-(5,5-dimethyl-2-oxo-morpholin-4-yl)-propyloxy]-7-methoxy-quinazoline (6) 4-[(3-Chloro-4-fluorophenyl)amino]-6-[2-(5,5-dimethyl-2-oxo-morpholin-4-yl)-ethoxy]-7-methoxy-quinazoline (7) 4-[(3-Chloro-4-fluorophenyl)amino]-6-[3-(3-methyl-2-oxo-morpholin-4-yl)-propyloxy]-7-methoxy-quinazoline (8) 4-[(3-Chloro-4-fluorophenyl)amino]-6-[2-(3-methyl-2-oxo-morpholin-4-yl)-ethoxy]-7-methoxy-quinazoline (9) 4-[(R)-(1-Phenyl-ethyl)amino]-6-[3-((R)-6-methyl-2-oxo-morpholin-4-yl)-propyloxy]-7-methoxy-quinazoline

(10) 4-[(R)-(1-Phenyl-ethyl)amino]-6-[2-((R)-6-methyl-2-oxo-morpholin-4-yl)-ethoxy]7-methoxy-quinazoline

(11) 4-[(3-Chloro-4-fluorophenyl)amino]-7-[4-(6-methyl-2-oxo-morpholin-4-yl)-butyloxy]-6-methoxy-quinazoline

(12) 4-[(3-Chloro-4-fluorophenyl)amino]-7-[3-(6-methyl-2-oxo-morpholin-4-yl)-propyloxy]-6-methoxy-quinazoline

(13) 4-[(3-Chloro-4-fluorophenyl)amino]-6-[4-(6-methyl-2-oxo-morpholin-4-yl)-butyloxy]-7-methoxy-quinazoline

(14) 4-[(3-Chloro-4-fluorophenyl)amino]-6-[2-(6-methyl-2-oxo-morpholin-4-yl)-ethoxy]-7-(tetrahydrofuran-3-yloxy)-quinazoline

(15) 4-[(3-Chloro-4-fluorophenyl)amino]-6-[2-(6-methyl-2-oxo-morpholin-4-yl)-ethoxy]-7-(tetrahydropyran-3-yloxy)-quinazoline

(16) 4-[(3-Chloro-4-fluorophenyl)amino]-6-[2-(6-methyl-2-oxo-morpholin-4-yl)-ethoxy]-7-(tetrahydropyran-4-yloxy)-quinazoline

(17) 4-[(3-Chloro-4-fluorophenyl)amino]-6-[2-(6-methyl-2-oxo-morpholin-4-yl)-ethoxy]-7-(tetrahydrofuran-2-ylmethoxy)-quinazoline

(18) 4-[(3-Chloro-4-fluorophenyl)amino]-6-[2-(6-methyl-2-oxo-morpholin-4-yl)-ethoxy]-7-(tetrahydropyran-4-ylmethoxy)-quinazoline

(19) 4-[(3-Chloro-4-fluorophenyl)amino]-6-[2-(6,6-dimethyl-2-oxo-morpholin-4-yl)-ethoxy]-7-(tetrahydrofuran-3-yloxy)-quinazoline

(20) 4-[(3-Chloro-4-fluorophenyl)amino]-6-[3-(6,6-dimethyl-2-oxo-morpholin-4-yl)-propyloxy]-7-(tetrahydrofuran-3-yloxy)-quinazoline

(21) 4-[(3-Chloro-4-fluorophenyl)amino]-6-[4-(6,6-dimethyl-2-oxo-morpholin-4-yl)-butyloxy]-7-(tetrahydrofuran-3-yloxy)-quinazoline

(22) 4-[(3-Chloro-4-fluorophenyl)amino]-6-[2-(6,6-dimethyl-2-oxo-morpholin-4-yl)-ethoxy]-7-(tetrahydrofuran-2-ylmethoxy)-quinazoline

(23) 4-[(3-Chloro-4-fluorophenyl)amino]-6-[3-(6,6-dimethyl-2-oxo-morpholin-4-yl)-propyloxy]-7-(tetrahydrofuran-2-ylmethoxy)-quinazoline

(24) 4-[(3-Chloro-4-fluorophenyl)amino]-6-[4-(6,6-dimethyl-2-oxo-morpholin-4-yl)-butyloxy]-7-(tetrahydrofuran-2-ylmethoxy)-quinazoline

(25) 4-[(3-Chloro-4-fluorophenyl)amino]-7-[2-(6-methyl-2-oxo-morpholin-4-yl)-ethoxy]-6-(tetrahydrofuran-3-yloxy)-quinazoline

(26) 4-[(3-Chloro-4-fluorophenyl)amino]-7-[2-(6-methyl-2-oxo-morpholin-4-yl)-ethoxy]-6-(tetrahydropyran-3-yloxy)-quinazoline

(27) 4-[(3-Chloro-4-fluorophenyl)amino]-7-[2-(6-methyl-2-oxo-morpholin-4-yl)-ethoxy]-6-(tetrahydropyran-4-yloxy)-quinazoline

(28) 4-[(3-Chloro-4-fluorophenyl)amino]-7-[2-(6-methyl-2-oxo-morpholin-4-yl)-ethoxy]-6-(tetrahydrofuran-2-ylmethoxy)-quinazoline

(29) 4-[(3-Chloro-4-fluorophenyl)amino]-7-[2-(6-methyl-2-oxo-morpholin-4-yl)-ethoxy]-6-(tetrahydropyran-4-ylmethoxy)-quinazoline

(30) 4-[(3-Chloro-4-fluorophenyl)amino]-7-[2-(6,6-dimethyl-2-oxo-morpholin-4-yl)-ethoxy]-6-(tetrahydrofuran-3-yloxy)-quinazoline

(31) 4-[(3-Chloro-4-fluorophenyl)amino]-7-[3-(6,6-dimethyl-2-oxo-morpholin-4-yl)-propyloxy]-6-(tetrahydrofuran-3-yloxy)-quinazoline

(32) 4-[(3-Chloro-4-fluorophenyl)amino]-7-[4-(6,6-dimethyl-2-oxo-morpholin-4-yl)-butyloxy]-6-(tetrahydrofuran-3-yloxy)-quinazoline

(33) 4-[(3-Chloro-4-fluorophenyl)amino]-7-[2-(6,6-dimethyl-2-oxo-morpholin-4-yl)-ethoxy]-6-(tetrahydrofuran-2-ylmethoxy)-quinazoline

(34) 4-[(3-Chloro-4-fluorophenyl)amino]-7-[3-(6,6-dimethyl-2-oxo-morpholin-4-yl)-propyloxy]-6-(tetrahydrofuran-2-ylmethoxy)-quinazoline

(35) 4-[(3-Chloro-4-fluorophenyl)amino]-7-[4-(6,6-dimethyl-2-oxo-morpholin-4-yl)-butyloxy]-6-(tetrahydrofuran-2-ylmethoxy)-quinazoline

EXAMPLE 5

Coated tablets containing 75 mg of active substance

| 1 tablet core contains: | |
| --- | --- |
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| Weight of core: | 230 mg |
| --- | --- |
| Die: | 9 mm, convex |

The tablet cores thus produced are coated with a film consisting essentially of hydroxypropylmethylcellulose. The finished film-coated tablets are polished with beeswax.

Weight of coated tablet: 245 mg.

EXAMPLE 6

Tablets containing 100 mg of active substance

| Composition: 1 tablet contains: | |
| --- | --- |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 7

Tablets containing 150 mg of active substance

| Composition: 1 tablet contains: | |
| --- | --- |
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE 8

Hard gelatine capsules containing 150 mg of active substance

| 1 capsule contains: | |
| --- | --- |
| active substance | 50.0 mg |
| corn starch (dried) approx. | 80.0 mg |
| lactose (powdered) approx. | 87.0 mg |
| magnesium stearate | 3.0 mg |
| approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE 9

Suppositories containing 150 mg of active substance

| 1 suppository contains: | |
| --- | --- |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 10

Suspension containing 50 mg of active substance

| 100 ml of suspension contain: | |
| --- | --- |
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 11

Ampoules containing 10 mg active substance

| Composition: | |
| --- | --- |
| active substance | 10.0 mg |
| 0.01 N hydrochloric acid q.s. | |
| double-distilled water ad | 2.0 ml |

Preparation:

The active substance is dissolved in the necessary amount of 0.01 N HCl, made isotonic with common salt, filtered sterile and transferred into 2 ml ampoules.

EXAMPLE 12

Ampoules containing 50 mg of active substance

| Composition: | |
| --- | --- |
| active substance | 50.0 mg |
| 0.01 N hydrochloric acid q.s. | |
| double-distilled water ad | 10.0 ml |

Preparation:

The active substance is dissolved in the necessary amount of 0.01 N HCl, made isotonic with common salt, filtered sterile and transferred into 10 ml ampoules.

EXAMPLE 13

Capsules for powder inhalation containing 5 mg of active substance

| 1 capsule contains: | |
|---|---|
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

weight of capsule: 70.0 mg
size of capsule=3

EXAMPLE 14

Solution for inhalation for hand-held nebulisers containing 2.5 mg active substance

| 1 spray contains: | |
|---|---|
| active substance | 2.500 mg |
| benzalkonium chloride | 0.001 mg |
| 1N hydrochloric acid q.s. | |
| ethanol/water (50/50) ad | 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).

Contents of the container: 4.5 g.

What is claimed is:

1. A compound of the formula I

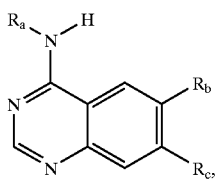

wherein:
$R_a$ is a 1-phenylethyl, 3-bromophenyl or 3-chloro-4-fluorophenyl group,
$R_b$ is a $R_3$—$(CH_2)_m$—O group, wherein
 $R_3$ is a 2-oxo-morpholin-4-yl group substituted by one or two methyl groups and m is the number 2 or 3,
 and $R_c$ is a methoxy, cyclobutyloxy, cyclopentyloxy, cyclopropylmethoxy, tetrahydrofuran-3-yloxy or tetrahydrofuranylmethoxy group, with the proviso that the compounds 4-[(3-bromo-phenyl)amino]-6-[2-(6,6-dimethyl-2-oxo-morpholin-4-yl)-ethoxy]-7-methoxy-quinazoline, 4-[(3-bromo-phenyl)amino]-6-[2-(3-methyl-2-oxo-morpholin-4-yl)ethoxy]-7-methoxy-quinazoline, 4-[(3-bromo-phenyl)amino]-6-[2-(5,5-dimethyl-2-oxo-morpholin-4-yl)ethoxy]-7-methoxy-quinazoline, 4-[(3-chloro-4-fluorophenyl)amino]-6-[2-(6,6-dimethyl-2-oxo-morpholin-4-yl)-ethoxy]-7-methoxy-quinazoline, 4-[(3-chloro-4-fluorophenyl)amino]-6-[2-(6,6-dimethyl-2-oxo-morpholin-4-yl)-ethoxy]-7-cyclobutyloxy-quinazoline, 4-[(3-chloro-4-fluorophenyl)amino]-6-[2-(6,6-dimethyl-2-oxo-morpholin-4-yl)-ethoxy]-7-cyclopropylmethoxy-quinazoline, 4-[(3-chloro-4-fluorophenyl)amino]-6-[3-(6,6-dimethyl-2-oxo-morpholin-4-yl)-propyloxy]-7-methoxy-quinazoline, 4-[(3-chloro-4-fluorophenyl)amino]-6-[2-(6,6-dimethyl-2-oxo-morpholin-4-yl)-ethoxy-7-cyclopentyloxy-quinazoline, 4-[(3-chloro-4-fluorophenyl)amino]-6-[3-(6,6-dimethyl-2-oxo-morpholin-4-yl)-propyloxy]-7-cyclopentyloxy-quinazoline and (R)-4-[(1-phenyl-ethyl)amino]-6-[3-(6,6-dimethyl-2-oxo-morpholin-4-yl)-propyloxy]-7-cyclopentyloxy-quinazoline are excluded, or a tautomer or salt thereof.

2. A compound selected from the group consisting of:

(4a) 4-[(3-chloro-4-fluorophenyl)amino]-7-cyclobutyloxy-6-[3-(6,6-dimethyl-2-oxo-morpholin-4-yl)-propyloxy]-quinazoline, (b) 4-[(3-chloro-4-fluorophenyl)amino]-7-cyclopropylmethoxy-6-[3-(6,6-dimethyl-2-oxo-morpholin-4-yl)-propyloxy]-quinazoline, (c) 4-[(3-bromo-phenyl)amino]-6-[2-((S)-6-methyl-2-oxo-morpholin-4-yl)-ethoxy]-]-7-methoxy-quinazoline, (d) 4-[(3-bromo-phenyl)amino]-6-[2-((R)-6-methyl-2-oxo-morpholin-4-yl)-ethoxy]-7-methoxy-quinazoline, (e) 4-[(3-chloro-4-fluorophenyl)amino]-6-[2-((R)-6-methyl-2-oxo-morpholin-4-yl)-ethoxy]-7-methoxy-quinazoline, (f) 4-[(3-chloro-4-fluorophenyl)amino]-6-[3-((R)-6-methyl-2-oxo-morpholin-4-yl)-propyloxy]-7-methoxy-quinazoline, (g) 4-[(R)-(1-phenyl-ethyl)amino]-6-[3-((S)-6-methyl-2-oxo-morpholin-4-yl)-propyloxy]-7-methoxy-quinazoline, (h) 4-[(R)-(1-phenyl-ethyl)amino]-6-[2-((S)-6-methyl-2-oxo-morpholin-4-yl)-ethoxy]-7-methoxy-quinazoline and (i) 4-[(3-chloro-4-fluorophenyl)amino]-6-[2-((S)-6-methyl-2-oxo-morpholin-4-yl)ethoxy]-7-methoxy-quinazoline, or a tautomer or salt thereof.

3. A physiologically acceptable salt of a compound according to claim 1, or 2 with inorganic or organic acid or base.

4. A pharmaceutical composition comprising a compound according to claim 1, or 2 or a physiologically acceptable salt thereof, and a pharmaceutically acceptable carrier or diluent.

5. A method for treating a disease of the airways or lungs which is accompanied by increased or altered production of mucus caused by stimulation by tyrosine kinase, which comprises administering to a host in need of such treatment a therapeutically effective amount of a compound according to claim 1 or 2 or a physiologically acceptable salt thereof.

6. The method of claim 5 wherein the disease is selected from the group consisting of chronic bronchitis, chronic obstructive bronchitis, asthma, bronchiectasis, allergic or non-allergic rhinitis or sinusitis, cystic fibrosis, α1-antitrypsin deficiency, cough, pulmonary emphysema, pulmonary fibrosis and hyperreactive airways.

* * * * *